US007598224B2

(12) United States Patent
Zamora et al.

(10) Patent No.: US 7,598,224 B2

(45) Date of Patent: Oct. 6, 2009

(54) DUAL CHAIN SYNTHETIC HEPARIN-BINDING GROWTH FACTOR ANALOGS

(75) Inventors: Paul O. Zamora, Gaithersburg, MD (US); Louis A. Pena, Poquott, NY (US); Xinhua Lin, Plainview, NY (US)

(73) Assignee: BioSurface Engineering Technologies, Inc., Rockville, MD (US)

(*) Notice: Subject to any disclaimer, the term of this patent is extended or adjusted under 35 U.S.C. 154(b) by 88 days.

(21) Appl. No.: 11/065,970

(22) Filed: Feb. 24, 2005

(65) Prior Publication Data

US 2005/0222394 A1 Oct. 6, 2005

Related U.S. Application Data

(63) Continuation-in-part of application No. 11/064,039, filed on Feb. 22, 2005, now Pat. No. 7,482,427, which is a continuation-in-part of application No. 10/644,703, filed on Aug. 19, 2003, which is a continuation-in-part of application No. 10/224,268, filed on Aug. 20, 2002.

(60) Provisional application No. 60/547,012, filed on Feb. 20, 2004.

(51) Int. Cl.

| | |
|---|---|
| ***A61K 38/00*** | (2006.01) |
| ***A61K 31/727*** | (2006.01) |
| ***A61K 38/24*** | (2006.01) |
| ***C07K 14/00*** | (2006.01) |
| ***C07K 16/00*** | (2006.01) |
| ***C08H 1/00*** | (2006.01) |

(52) U.S. Cl. .......................... 514/18; 514/56; 530/300; 530/397; 530/399; 530/402

(58) Field of Classification Search ...................... None

See application file for complete search history.

(56) References Cited

U.S. PATENT DOCUMENTS

| | | | |
|---|---|---|---|
| 4,172,128 | A | 10/1979 | Thiele et al. |
| 4,563,350 | A | 1/1986 | Nathan et al. |
| 5,563,046 | A | 10/1996 | Mascarenhas et al. |
| 5,608,035 | A | 3/1997 | Yanofsky et al. |
| 5,635,597 | A | 6/1997 | Barrett et al. |
| 5,643,873 | A | 7/1997 | Barrett et al. |
| 5,648,458 | A | 7/1997 | Cwirla et al. |
| 5,654,276 | A | 8/1997 | Barrett et al. |
| 5,668,110 | A | 9/1997 | Barrett et al. |
| 5,674,977 | A | 10/1997 | Gariepy |
| 5,679,637 | A | 10/1997 | Lappi et al. |
| 5,679,673 | A | 10/1997 | Bowen et al. |
| 5,684,136 | A | 11/1997 | Godowski |
| 5,728,802 | A | 3/1998 | Barrett et al. |
| 5,759,515 | A | 6/1998 | Rhodes et al. |
| 5,767,234 | A | 6/1998 | Yanofsky et al. |
| 5,770,704 | A | 6/1998 | Godowski |
| 5,773,569 | A | 6/1998 | Wrighton et al. |
| 5,786,322 | A | 7/1998 | Barrett et al. |
| 5,786,331 | A | 7/1998 | Barrett et al. |
| 5,789,182 | A | 8/1998 | Yayon et al. |
| 5,830,851 | A | 11/1998 | Wrighton et al. |
| 5,861,476 | A | 1/1999 | Barrett et al. |
| 5,866,113 | A | 2/1999 | Hendriks et al. |
| 5,869,451 | A | 2/1999 | Dower et al. |
| 5,880,096 | A | 3/1999 | Barrett et al. |
| 5,902,799 | A | 5/1999 | Herrmann et al. |
| 5,932,462 | A | 8/1999 | Harris et al. |
| 5,952,474 | A | 9/1999 | Kayman et al. |
| 5,955,588 | A | 9/1999 | Tsang et al. |
| 5,965,532 | A | 10/1999 | Bachovchin |
| 5,989,866 | A | 11/1999 | Deisher et al. |
| 5,994,104 | A | 11/1999 | Anderson et al. |
| 6,001,364 | A | 12/1999 | Rose et al. |
| 6,011,002 | A | 1/2000 | Pastan et al. |
| 6,030,812 | A | 2/2000 | Bauer et al. |
| 6,051,648 | A | 4/2000 | Rhee et al. |
| 6,121,236 | A | 9/2000 | Ben-Sasson |
| 6,168,784 | B1 | 1/2001 | Offord et al. |
| 6,174,530 | B1 | 1/2001 | Rose et al. |
| 6,174,721 | B1 | 1/2001 | Innis et al. |
| 6,214,795 | B1 | 4/2001 | Benjamin et al. |
| 6,217,873 | B1 | 4/2001 | Rose et al. |
| 6,235,716 | B1 | 5/2001 | Ben-Sasson |
| 6,251,864 | B1 | 6/2001 | Dower et al. |
| 6,284,503 | B1 | 9/2001 | Caldwell et al. |
| 6,294,359 | B1 | 9/2001 | Fiddes et al. |
| 6,323,323 | B1 | 11/2001 | Sledziewski et al. |

(Continued)

FOREIGN PATENT DOCUMENTS

| | | |
|---|---|---|
| WO | WO-00/18921 | 4/2000 |
| WO | WO-02/04015 | 1/2002 |
| WO | WO-02/20033 | 3/2002 |
| WO | WO-0219963 | 3/2002 |
| WO | WO-02/062823 | 8/2002 |

OTHER PUBLICATIONS

Bork et al., Go hunting in sequence databases but watch out for the traps, 1996, Trends in Genetics, vol. 12, pp. 425-427.*

(Continued)

*Primary Examiner*—Robert Landsman
*Assistant Examiner*—Ian Dang
(74) *Attorney, Agent, or Firm*—Janeen Vilven; Peacock Myers, P.C.

(57) ABSTRACT

The invention provides synthetic heparin-binding growth factor analogs having two peptide chains each branched from a branch moiety, such as trifunctional amino acid residues, the branch moieties separated by a first linker of from 3 to about 20 backbone atoms, which peptide chains bind a heparin-binding growth factor receptor and are covalently bound to a non-signaling peptide that includes a heparin-binding domain, preferably by a second linker, which may be a hydrophobic second linker. The synthetic heparin-binding growth factor analogs are useful as pharmaceutical agents, soluble biologics or as surface coatings for medical devices.

9 Claims, No Drawings

U.S. PATENT DOCUMENTS

| | | | |
|---|---|---|---|
| 6,326,468 | B1 | 12/2001 | Canne et al. |
| 6,342,591 | B1 | 1/2002 | Zamora et al. |
| 6,350,731 | B1 | 2/2002 | Jehanli et al. |
| 6,377,349 | B1 | 4/2002 | Fercher |
| 6,451,543 | B1 | 9/2002 | Kochendoerfer et al. |
| 2003/0224996 | A1 | 12/2003 | Opperman et al. |

OTHER PUBLICATIONS

Bork, Powers and Pitfalls in Sequence Analysis: the 70% hurdle, 2000, Genome Research, vol. 10, pp. 398-400.*

Brenner, Errors in genome annotation, 1999, Trends in Genetics, vol. 15, pp. 132-132.*

Doerks et al., Protein annotation: detective work for function prediction, 1998, Trends in Genetics, vol. 14, pp. 248-250.*

Ngo et al., The protein folding problem and tertiary structure prediction,1994, pp. 492-495.*

Skolnick et al., From genes to protein structure and function: novel applications of computational approaches in the genomic era, 2000, Trends in Biotech, vol. 18, Issue 1, pp. 34-39.*

Smith et al., The challenge of genome sequence annotation or "the devil is in the details", 1997, Nature Biotechnology, vol. 15, pp. 1222-1223.*

Wells et al., Addivity of mutational effects in proteins, 1990, Biochemistry, vol. 29, pp. 8509-8517.*

Ahmed, Asif, et al., "Role of VEFGF Receptor-1 (Fit-1) in Mediating Calcium-Dependent Nitric Oxide Release and Limiting DNA Synthesis in Human Trophoblast Cells", *Lab Invest.*, vol. 76(6), (Jun. 1977),779-791.

Andrades, Jose A., et al., "A Recombinant Human TGF-B1 Fusion Protein with Collagen-Binding Domain Promostes Migration, Growth, and Differentiation of Bone Marrow Mesenchymal Cells", *Experimental Cell Research*, (1999),485-498.

Ballinger, Marcus D., et al., "Semirational design of a potent, artificial agonist of fibroblast growth factor receptors", *Nature Biotechnology*, (1999),1199-1204.

Binetruy-Tournaire, Roselyne, et al., "Identification of a Peptide Blocking Vascular Endothelial Growth Factor (VEGF)-mediated Angiogenesis", *The EMBO Journal*, vol. 19, No. 7, (2000),1525-1533.

Brennand, David M., et al., "Identification of a Cyclic Peptide Inhibitor of Platelet-Derived Growth Factor-BB Receptor-Binding and Mitogen-Induced DNA Synthesis in Human Fibroblasts", *FEBS Letters*, 413, (1997),70-74.

Carmeliet, Peter, et al., "Growing Better Blood Vessels" , *Nature Biotechnology*, (2001),1019-1020.

Dawson, Philip E., et al., "Synthesis of Native Proteins by Chemical Ligation", *Annu. Rev. Biochem*, 2000, 69, (2000),923-960.

Dikov, Michael M., et al., "A Functional Fibroblast Growth Factor-1 Immunoglobulin Fusion Protein", *The Journal of Biological Chemistry*, (1998),15811-15817.

Engstrom, Ulla, et al., "Identification of a Peptide Antagonist for Platelet-Derived Growth Factor", *The Journal of Biological Chemistry*, vol. 273, No. 25, (1998),15811-15817.

Eom, Khee D., et al., "Tandem Ligation of Multipartite Peptides with Cell-Permeable Activity", *J. Am. Chem. Soc.*, 2003,125, (2003),73-83.

Gay, Cyril G., et al., "Interleukin 1 regulated heparin-binding growth factor 2 gene expression in vascular smooth muscle cells", *Proc. Natl. Acad. Sci. USA*, vol. 88, (Jan. 1991),296-300.

Hasan, Maemunah, et al., "IL-12 is a Heparin-Binding Cytokine", *The Journal of Immunology*, (1999), 1064-1070.

Hoke, David E., et al., "A Heparin Binding Synthetic Peptide from Human HIP/RPL29 Fails to Specifically Differentiate Between Anticoagulantly Active and Inactive Species of Heparin", *Journal of Negative Results in BioMedicine*, (2003).

Kochendoefer, Gerd, et al., "Design and Chemical Synthesis of Homogenous Polymer-Modified Erythropotesis Protein", *Science*, vol. 299, (Feb. 7, 2003).

Ostman, Arne, et al., "Identification of Three Amino Acids in the Platelet-Derived Growth Factor (PDGF) B-chain that are Important for Binding to the PDGF B-Receptor", *The Journal of Biological Chemistry*, vol. 266, No. 16, Issue of Jun. 5, (1991),10073-10077.

Paris, Francois, et al., "Endothelial Apoptosis as the Primary Lesion Initiating Intestinal Radiation Damage in Mice", *Science*, (2001),293-297.

Pellegrini, Luca, "Role of heparan sulfate in fibroblast growth factor signaling a structural view", *Structural Biology*, (2001),629-634.

Ray, Jasohara, et al., "A 10-amino acid sequence of fibroblast growth factor 2 is sufficient for its mitogenic activity on neural progenitor cells", *Proc. Natl. Acad. Sci. USA*, (1997),7047-7052.

Richardson, Thomas P., et al., "Polymeric system for dual growth factor delivery", *Nature Biotechnology*, (2001),293-297.

Rusnati, Marco, et al., "avB3 Integrin Mediates the Cell-adhesive Capacity and Biological Activity of Basic Fibroblast Growth Factor (FGF-2) in Cultured Endothelial Cells", *Molecular Biology of the Cell*, (1997),2449-2461.

Sood, R., et al., "MDS1/EVI1 enhances TGF-B1 signaling and strengthens its growth-inhibitory effect, but the leukemia-associated fusion protein AML1/MDS1/EVI1, product of the t(3:21), abrogates growth-inhibition in response to TGF-B1", *Leukemia*, (1999),348-357.

Takizawa, Takuma, et al., "Directly Linked Soluble IL-6 Receptor-IL-6 Fusion Protein Induces Astrocyte Differentiation from Neuroepithelial Cells Via Activation of STAT3", *Cytokine*, (2001),272-279.

Verrecchio, Angela, "Design of Peptides with High Affinities for Heparin and Endothelial Cell Proteoglycans", *The Journal of Biological Chemistry*, vol. 275, No. 11, (Mar. 17, 2000),7701-7707.

Yoneda, Atsuko, "Engineering of an FGF-proteoglycan fusion protein with heparin-independent, mitogenic activity", *Nature Biotechnology* vol. 18, (Jun. 2000),641-644.

Yoneda, Atsuko, et al., "Engineering of an FGF-proteoglycan fusion protein with heparin-independent, mitogenic activity", *Nature Biotechnology*, (2000),641-644.

Ray, Jasohara et al., "A 10-amino acid sequence of fibroblast growth factor 2 is sufficient for its mitogenic activity on neural progenitor cells", *Proc. Natl. Acad. Sci. USA* 1997, 7047-7052.

Shen, Wei-Chiang et al., "Poly(l-lysine) has different membrane transport and drug-carrier properties when complexed with heparin", *Proc Natl Acad Sci USA* Dec. 1981, 7589-93.

Tanaka, H. et al., "Involvement of bone morphogenic protein-2 (BMP-2) in the pathological ossification process of the spinal ligament", *Rheumatology 2001*;40 May 9, 2001, 1163-1168.

* cited by examiner

SEQUENCE LISTING

<160> NUMBER OF SEQ ID NOS: 65

<210> SEQ ID NO 1
<211> LENGTH: 6
<212> TYPE: PRT
<213> ORGANISM: Artificial
<220> FEATURE:
<223> OTHER INFORMATION: artificial heparin-binding sequence
<220> FEATURE:
<221> NAME/KEY: MISC_FEATURE
<222> LOCATION: (1)..(3)
<223> OTHER INFORMATION: where each Xaa is independently lysine or arginine
<220> FEATURE:
<221> NAME/KEY: MISC_FEATURE
<222> LOCATION: (4)..(5)
<223> OTHER INFORMATION: where each Xaa is independently any amino acid residue
<220> FEATURE:
<221> NAME/KEY: MISC_FEATURE
<222> LOCATION: (6)..(6)
<223> OTHER INFORMATION: where Xaa is lysine or arginine

<400> SEQUENCE: 1

```
Xaa Xaa Xaa Xaa Xaa Xaa
1               5
```

<210> SEQ ID NO 2
<211> LENGTH: 10
<212> TYPE: PRT
<213> ORGANISM: Artificial
<220> FEATURE:
<223> OTHER INFORMATION: synthetic heparin-binding sequence

<400> SEQUENCE: 2

```
Arg Lys Arg Lys Leu Glu Arg Ile Ala Arg
1               5                   10
```

<210> SEQ ID NO 3
<211> LENGTH: 10
<212> TYPE: PRT
<213> ORGANISM: Artificial
<220> FEATURE:
<223> OTHER INFORMATION: synthetic heparin-binding sequence

<400> SEQUENCE: 3

```
Arg Lys Arg Lys Leu Gly Arg Ile Ala Arg
1               5                   10
```

<210> SEQ ID NO 4
<211> LENGTH: 10
<212> TYPE: PRT
<213> ORGANISM: Artificial
<220> FEATURE:
<223> OTHER INFORMATION: synthetic heparin-binding sequence

<400> SEQUENCE: 4

```
Arg Lys Arg Lys Leu Trp Arg Ala Arg Ala
1               5                   10
```

<210> SEQ ID NO 5
<211> LENGTH: 9
<212> TYPE: PRT
<213> ORGANISM: Artificial
<220> FEATURE:

-continued

```
<223> OTHER INFORMATION: synthetic heparin-binding sequence

<400> SEQUENCE: 5

Arg Lys Arg Leu Asp Arg Ile Ala Arg
1               5


<210> SEQ ID NO 6
<211> LENGTH: 11
<212> TYPE: PRT
<213> ORGANISM: Artificial
<220> FEATURE:
<223> OTHER INFORMATION: synthetic heparin-binding sequence

<400> SEQUENCE: 6

Arg Lys Arg Lys Leu Glu Arg Ile Ala Arg Cys
1               5                   10


<210> SEQ ID NO 7
<211> LENGTH: 15
<212> TYPE: PRT
<213> ORGANISM: Artificial
<220> FEATURE:
<223> OTHER INFORMATION: synthetic FGF-2 analog

<400> SEQUENCE: 7

Tyr Arg Ser Arg Lys Tyr Thr Ser Trp Tyr Val Ala Leu Lys Arg
1               5                   10                  15


<210> SEQ ID NO 8
<211> LENGTH: 28
<212> TYPE: PRT
<213> ORGANISM: Artificial
<220> FEATURE:
<223> OTHER INFORMATION: synthetic FGF-2 analog

<400> SEQUENCE: 8

Asn Arg Phe His Ser Trp Asp Cys Ile Lys Thr Trp Ala Ser Asp Thr
1               5                   10                  15

Phe Val Leu Val Cys Tyr Asp Asp Gly Ser Glu Ala
            20                  25


<210> SEQ ID NO 9
<211> LENGTH: 15
<212> TYPE: PRT
<213> ORGANISM: Artificial
<220> FEATURE:
<223> OTHER INFORMATION: synthetic FGF-2 analog

<400> SEQUENCE: 9

His Ile Lys Leu Gln Leu Gln Ala Glu Glu Arg Gly Val Val Ser
1               5                   10                  15


<210> SEQ ID NO 10
<211> LENGTH: 17
<212> TYPE: PRT
<213> ORGANISM: Artificial
<220> FEATURE:
<223> OTHER INFORMATION: synthetic FGF-1 analog

<400> SEQUENCE: 10

Tyr Ile Ser Lys Lys His Ala Glu Lys Asn Trp Phe Val Gly Leu Lys
1               5                   10                  15

Lys
```

-continued

<210> SEQ ID NO 11
<211> LENGTH: 15
<212> TYPE: PRT
<213> ORGANISM: Artificial
<220> FEATURE:
<223> OTHER INFORMATION: synthetic FGF-1 analog

<400> SEQUENCE: 11

His Ile Gln Leu Gln Leu Ser Ala Glu Ser Val Gly Glu Val Tyr
1               5                   10                  15

<210> SEQ ID NO 12
<211> LENGTH: 20
<212> TYPE: PRT
<213> ORGANISM: Artificial
<220> FEATURE:
<223> OTHER INFORMATION: synthetic FGF-7 analog

<400> SEQUENCE: 12

Tyr Ala Ser Ala Lys Trp Thr His Asn Gly Gly Glu Met Phe Val Ala
1               5                   10                  15

Leu Asn Gln Lys
            20

<210> SEQ ID NO 13
<211> LENGTH: 15
<212> TYPE: PRT
<213> ORGANISM: Artificial
<220> FEATURE:
<223> OTHER INFORMATION: synthetic FGF-7 analog

<400> SEQUENCE: 13

Tyr Asn Ile Met Glu Ile Arg Thr Val Ala Val Gly Ile Val Ala
1               5                   10                  15

<210> SEQ ID NO 14
<211> LENGTH: 20
<212> TYPE: PRT
<213> ORGANISM: Artificial
<220> FEATURE:
<223> OTHER INFORMATION: synthetic FGF-10 analog

<400> SEQUENCE: 14

Tyr Ala Ser Phe Asn Trp Gln His Asn Gly Arg Gln Met Tyr Val Ala
1               5                   10                  15

Leu Asn Gln Lys
            20

<210> SEQ ID NO 15
<211> LENGTH: 19
<212> TYPE: PRT
<213> ORGANISM: Artificial
<220> FEATURE:
<223> OTHER INFORMATION: synthetic FGF-22 analog

<400> SEQUENCE: 15

Tyr Ala Ser Gln Arg Trp Arg Arg Arg Gly Gln Pro Asn Leu Ala Leu
1               5                   10                  15

Asp Arg Arg

<210> SEQ ID NO 16
<211> LENGTH: 21

-continued

<212> TYPE: PRT
<213> ORGANISM: Artificial
<220> FEATURE:
<223> OTHER INFORMATION: synthetic FGF-9 analog

<400> SEQUENCE: 16

Tyr Ser Ser Asn Leu Tyr Lys His Val Asp Thr Gly Arg Arg Tyr Tyr
1 5 10 15

Val Ala Leu Asn Lys
20

<210> SEQ ID NO 17
<211> LENGTH: 20
<212> TYPE: PRT
<213> ORGANISM: Artificial
<220> FEATURE:
<223> OTHER INFORMATION: synthetic FGF-16 analog

<400> SEQUENCE: 17

Tyr Ala Ser Thr Leu Tyr Lys His Ser Asp Ser Glu Arg Gln Tyr Val
1 5 10 15

Ala Leu Asn Lys
20

<210> SEQ ID NO 18
<211> LENGTH: 20
<212> TYPE: PRT
<213> ORGANISM: Artificial
<220> FEATURE:
<223> OTHER INFORMATION: synthetic FGF-20 analog

<400> SEQUENCE: 18

Tyr Ser Ser Asn Ile Tyr Lys His Gly Asp Thr Gly Arg Arg Phe Val
1 5 10 15

Ala Leu Asn Lys
20

<210> SEQ ID NO 19
<211> LENGTH: 16
<212> TYPE: PRT
<213> ORGANISM: Artificial
<220> FEATURE:
<223> OTHER INFORMATION: synthetic FGF-4 analog

<400> SEQUENCE: 19

Tyr Glu Ser Tyr Lys Tyr Pro Gly Met Phe Ile Ala Leu Ser Lys Asn
1 5 10 15

<210> SEQ ID NO 20
<211> LENGTH: 17
<212> TYPE: PRT
<213> ORGANISM: Artificial
<220> FEATURE:
<223> OTHER INFORMATION: synthetic FGF-6 analog

<400> SEQUENCE: 20

Tyr Glu Ser Asp Leu Tyr Gln Gly Thr Tyr Ile Leu Ser Lys Tyr Gly
1 5 10 15

Arg

<210> SEQ ID NO 21
<211> LENGTH: 20
<212> TYPE: PRT

-continued

<213> ORGANISM: Artificial
<220> FEATURE:
<223> OTHER INFORMATION: synthetic FGF-12 analog

<400> SEQUENCE: 21

Tyr Ser Ser Thr Leu Tyr Arg Gln Gln Glu Ser Gly Arg Ala Trp Phe
1 5 10 15

Leu Gly Asn Lys
20

<210> SEQ ID NO 22
<211> LENGTH: 21
<212> TYPE: PRT
<213> ORGANISM: Artificial
<220> FEATURE:
<223> OTHER INFORMATION: synthetic FGF-14 analog

<400> SEQUENCE: 22

Tyr Ser Ser Met Leu Tyr Arg Gln Gln Glu Ser Gly Arg Ala Trp Phe
1 5 10 15

Leu Gly Leu Asn Lys
20

<210> SEQ ID NO 23
<211> LENGTH: 21
<212> TYPE: PRT
<213> ORGANISM: Artificial
<220> FEATURE:
<223> OTHER INFORMATION: synthetic FGF-13 analog

<400> SEQUENCE: 23

Tyr Ser Ser Met Ile Tyr Arg Gln Gln Gln Ser Gly Arg Gly Trp Tyr
1 5 10 15

Leu Gly Leu Asn Lys
20

<210> SEQ ID NO 24
<211> LENGTH: 19
<212> TYPE: PRT
<213> ORGANISM: Artificial
<220> FEATURE:
<223> OTHER INFORMATION: synthetic FGF-11 analog

<400> SEQUENCE: 24

Tyr Ala Ser Ala Leu Tyr Arg Gln Arg Arg Ser Gly Arg Ala Trp Tyr
1 5 10 15

Leu Asp Lys

<210> SEQ ID NO 25
<211> LENGTH: 20
<212> TYPE: PRT
<213> ORGANISM: Artificial
<220> FEATURE:
<223> OTHER INFORMATION: synthetic VEGF analog

<400> SEQUENCE: 25

Ala Pro Met Ala Glu Gly Gly Gly Gln Asn His His Glu Val Val Lys
1 5 10 15

Phe Met Asp Val
20

<210> SEQ ID NO 26
<211> LENGTH: 11
<212> TYPE: PRT

-continued

<213> ORGANISM: Artificial
<220> FEATURE:
<223> OTHER INFORMATION: synthetic VEGF analog

<400> SEQUENCE: 26

Gly Ala Thr Trp Leu Pro Pro Asn Pro Thr Lys
1 5 10

<210> SEQ ID NO 27
<211> LENGTH: 20
<212> TYPE: PRT
<213> ORGANISM: Artificial
<220> FEATURE:
<223> OTHER INFORMATION: synthetic VEGF analog

<400> SEQUENCE: 27

Asn Phe Leu Leu Ser Trp Val His Trp Ser Leu Ala Leu Leu Leu Tyr
1 5 10 15

Leu His His Ala
20

<210> SEQ ID NO 28
<211> LENGTH: 13
<212> TYPE: PRT
<213> ORGANISM: Artificial
<220> FEATURE:
<223> OTHER INFORMATION: synthetic BMP analog

<400> SEQUENCE: 28

Leu Tyr Val Asp Phe Ser Asp Val Gly Trp Asn Asp Trp
1 5 10

<210> SEQ ID NO 29
<211> LENGTH: 15
<212> TYPE: PRT
<213> ORGANISM: Artificial
<220> FEATURE:
<223> OTHER INFORMATION: synthetic BMP analog

<400> SEQUENCE: 29

Ala Ile Ser Met Leu Tyr Leu Asp Glu Asn Glu Lys Val Val Leu
1 5 10 15

<210> SEQ ID NO 30
<211> LENGTH: 17
<212> TYPE: PRT
<213> ORGANISM: Artificial
<220> FEATURE:
<223> OTHER INFORMATION: synthetic BMP analog

<400> SEQUENCE: 30

Ile Ser Met Leu Tyr Leu Asp Glu Asn Glu Lys Val Val Leu Lys Asn
1 5 10 15

Tyr

<210> SEQ ID NO 31
<211> LENGTH: 15
<212> TYPE: PRT
<213> ORGANISM: Artificial
<220> FEATURE:
<223> OTHER INFORMATION: synthetic BMP analog

<400> SEQUENCE: 31

Glu Lys Val Val Leu Lys Asn Tyr Gln Asp Met Val Val Glu Gly
1 5 10 15

-continued

<210> SEQ ID NO 32
<211> LENGTH: 16
<212> TYPE: PRT
<213> ORGANISM: Artificial
<220> FEATURE:
<223> OTHER INFORMATION: synthetic BMP analog

<400> SEQUENCE: 32

Leu Val Val Lys Glu Asn Glu Asp Leu Tyr Leu Met Ser Ile Ala Cys
1               5                   10                  15

<210> SEQ ID NO 33
<211> LENGTH: 16
<212> TYPE: PRT
<213> ORGANISM: Artificial
<220> FEATURE:
<223> OTHER INFORMATION: synthetic BMP analog

<400> SEQUENCE: 33

Ala Phe Tyr Cys His Gly Glu Cys Pro Phe Pro Leu Ala Asp His Leu
1               5                   10                  15

<210> SEQ ID NO 34
<211> LENGTH: 23
<212> TYPE: PRT
<213> ORGANISM: Artificial
<220> FEATURE:
<223> OTHER INFORMATION: synthetic BMP analog

<400> SEQUENCE: 34

Pro Phe Pro Leu Ala Asp His Leu Asn Ser Thr Asn His Ala Ile Val
1               5                   10                  15

Gln Thr Leu Val Asn Ser Val
            20

<210> SEQ ID NO 35
<211> LENGTH: 21
<212> TYPE: PRT
<213> ORGANISM: Artificial
<220> FEATURE:
<223> OTHER INFORMATION: synthetic TGF-beta1 analog

<400> SEQUENCE: 35

Ile Val Tyr Tyr Val Gly Arg Lys Pro Lys Val Glu Gln Leu Ser Asn
1               5                   10                  15

Met Ile Val Arg Ser
            20

<210> SEQ ID NO 36
<211> LENGTH: 22
<212> TYPE: PRT
<213> ORGANISM: Artificial
<220> FEATURE:
<223> OTHER INFORMATION: synthetic TGF-beta2 analog

<400> SEQUENCE: 36

Thr Ile Leu Tyr Tyr Ile Gly Lys Thr Pro Lys Ile Glu Gln Leu Ser
1               5                   10                  15

Asn Met Ile Val Lys Ser
            20

<210> SEQ ID NO 37
<211> LENGTH: 21
<212> TYPE: PRT
<213> ORGANISM: Artificial

-continued

```
<220> FEATURE:
<223> OTHER INFORMATION: synthetic TGF-beta3 analog

<400> SEQUENCE: 37

Leu Thr Ile Leu Tyr Tyr Val Gly Arg Thr Pro Lys Val Glu Gln Leu
1               5                   10                  15

Ser Asn Met Val Val
            20


<210> SEQ ID NO 38
<211> LENGTH: 23
<212> TYPE: PRT
<213> ORGANISM: Artificial
<220> FEATURE:
<223> OTHER INFORMATION: synthetic BMP-2 analog

<400> SEQUENCE: 38

Ala Ile Ser Met Leu Tyr Leu Asp Glu Asn Glu Lys Val Val Leu Lys
1               5                   10                  15

Asn Tyr Gln Asp Met Val Val
            20


<210> SEQ ID NO 39
<211> LENGTH: 24
<212> TYPE: PRT
<213> ORGANISM: Artificial
<220> FEATURE:
<223> OTHER INFORMATION: synthetic BMP-3 analog

<400> SEQUENCE: 39

Ser Ser Leu Ser Ile Leu Phe Phe Asp Glu Asn Lys Asn Val Val Leu
1               5                   10                  15

Lys Val Tyr Pro Asn Met Thr Val
            20


<210> SEQ ID NO 40
<211> LENGTH: 24
<212> TYPE: PRT
<213> ORGANISM: Artificial
<220> FEATURE:
<223> OTHER INFORMATION: synthetic BMP-3beta analog

<400> SEQUENCE: 40

Asn Ser Leu Gly Val Leu Phe Leu Asp Glu Asn Arg Asn Val Val Leu
1               5                   10                  15

Lys Val Tyr Pro Asn Met Ser Val
            20


<210> SEQ ID NO 41
<211> LENGTH: 23
<212> TYPE: PRT
<213> ORGANISM: Artificial
<220> FEATURE:
<223> OTHER INFORMATION: synthetic BMP-4 analog

<400> SEQUENCE: 41

Ala Ile Ser Met Leu Tyr Leu Asp Glu Tyr Asp Lys Val Val Leu Lys
1               5                   10                  15

Asn Tyr Gln Glu Met Val Val
            20


<210> SEQ ID NO 42
<211> LENGTH: 23
<212> TYPE: PRT
```

-continued

<213> ORGANISM: Artificial
<220> FEATURE:
<223> OTHER INFORMATION: synthetic BMP-5 analog

<400> SEQUENCE: 42

```
Ala Ile Ser Val Leu Tyr Phe Asp Asp Ser Ser Asn Val Ile Leu Lys
1               5                   10                  15

Lys Tyr Arg Asn Met Val Val
            20
```

<210> SEQ ID NO 43
<211> LENGTH: 23
<212> TYPE: PRT
<213> ORGANISM: Artificial
<220> FEATURE:
<223> OTHER INFORMATION: synthetic BMP-6 analog

<400> SEQUENCE: 43

```
Ala Ile Ser Val Leu Tyr Phe Asp Asp Asn Ser Asn Val Ile Leu Lys
1               5                   10                  15

Lys Tyr Arg Asn Met Val Val
            20
```

<210> SEQ ID NO 44
<211> LENGTH: 23
<212> TYPE: PRT
<213> ORGANISM: Artificial
<220> FEATURE:
<223> OTHER INFORMATION: synthetic BMP-7 analog

<400> SEQUENCE: 44

```
Ala Ile Ser Val Leu Tyr Phe Asp Asp Ser Ser Asn Val Ile Leu Lys
1               5                   10                  15

Lys Tyr Arg Asn Met Val Val
            20
```

<210> SEQ ID NO 45
<211> LENGTH: 23
<212> TYPE: PRT
<213> ORGANISM: Artificial
<220> FEATURE:
<223> OTHER INFORMATION: synthetic BMP-8 analog

<400> SEQUENCE: 45

```
Ala Thr Ser Val Leu Tyr Tyr Asp Ser Ser Asn Asn Val Ile Leu Arg
1               5                   10                  15

Lys Ala Arg Asn Met Val Val
            20
```

<210> SEQ ID NO 46
<211> LENGTH: 23
<212> TYPE: PRT
<213> ORGANISM: Artificial
<220> FEATURE:
<223> OTHER INFORMATION: synthetic BMP-9 analog

<400> SEQUENCE: 46

```
Ile Ser Val Leu Tyr Lys Asp Asp Met Gly Val Pro Thr Leu Lys Tyr
1               5                   10                  15

His Tyr Glu Gly Met Ser Val
            20
```

<210> SEQ ID NO 47
<211> LENGTH: 22

-continued

<212> TYPE: PRT
<213> ORGANISM: Artificial
<220> FEATURE:
<223> OTHER INFORMATION: synthetic BMP-10 analog

<400> SEQUENCE: 47

Ile Ser Ile Leu Tyr Leu Asp Lys Gly Val Val Thr Tyr Lys Phe Lys
1 5 10 15

Tyr Glu Gly Met Ala Val
20

<210> SEQ ID NO 48
<211> LENGTH: 22
<212> TYPE: PRT
<213> ORGANISM: Artificial
<220> FEATURE:
<223> OTHER INFORMATION: synthetic BMP-11 analog

<400> SEQUENCE: 48

Ile Asn Met Leu Tyr Phe Asn Asp Lys Gln Gln Ile Ile Tyr Gly Lys
1 5 10 15

Ile Pro Gly Met Val Val
20

<210> SEQ ID NO 49
<211> LENGTH: 22
<212> TYPE: PRT
<213> ORGANISM: Artificial
<220> FEATURE:
<223> OTHER INFORMATION: synthetic BMP-12 analog

<400> SEQUENCE: 49

Ile Ser Ile Leu Tyr Ile Asp Ala Ala Asn Asn Val Val Tyr Lys Gln
1 5 10 15

Tyr Glu Asp Met Val Val
20

<210> SEQ ID NO 50
<211> LENGTH: 22
<212> TYPE: PRT
<213> ORGANISM: Artificial
<220> FEATURE:
<223> OTHER INFORMATION: synthetic BMP-13 analog

<400> SEQUENCE: 50

Ile Ser Ile Leu Tyr Ile Asp Ala Gly Asn Asn Val Val Tyr Lys Gln
1 5 10 15

Tyr Glu Asp Met Val Val
20

<210> SEQ ID NO 51
<211> LENGTH: 22
<212> TYPE: PRT
<213> ORGANISM: Artificial
<220> FEATURE:
<223> OTHER INFORMATION: synthetic BMP-14 analog

<400> SEQUENCE: 51

Ile Ser Ile Leu Phe Ile Asp Ser Ala Asn Asn Val Val Tyr Lys Gln
1 5 10 15

Tyr Glu Asp Met Val Val
20

<210> SEQ ID NO 52

-continued

```
<211> LENGTH: 22
<212> TYPE: PRT
<213> ORGANISM: Artificial
<220> FEATURE:
<223> OTHER INFORMATION: synthetic BMP-15 analog

<400> SEQUENCE: 52

Ile Ser Val Leu Met Ile Glu Ala Asn Gly Ser Ile Leu Tyr Lys Glu
1               5                   10                  15

Tyr Glu Gly Met Ile Ala
            20


<210> SEQ ID NO 53
<211> LENGTH: 22
<212> TYPE: PRT
<213> ORGANISM: Artificial
<220> FEATURE:
<223> OTHER INFORMATION: synthetic GDF-1 analog

<400> SEQUENCE: 53

Ile Ser Val Leu Phe Phe Asp Asn Ser Asp Asn Val Val Leu Arg Gln
1               5                   10                  15

Tyr Glu Asp Met Val Val
            20


<210> SEQ ID NO 54
<211> LENGTH: 22
<212> TYPE: PRT
<213> ORGANISM: Artificial
<220> FEATURE:
<223> OTHER INFORMATION: synthetic GDF-3 analog

<400> SEQUENCE: 54

Ile Ser Met Leu Tyr Gln Asp Asn Asn Asp Asn Val Ile Leu Arg His
1               5                   10                  15

Tyr Glu Asp Met Val Val
            20


<210> SEQ ID NO 55
<211> LENGTH: 22
<212> TYPE: PRT
<213> ORGANISM: Artificial
<220> FEATURE:
<223> OTHER INFORMATION: synthetic GDF-8 analog

<400> SEQUENCE: 55

Ile Asn Met Tyr Leu Phe Asn Gly Lys Glu Gln Ile Ile Tyr Gly Lys
1               5                   10                  15

Ile Pro Ala Met Val Val
            20


<210> SEQ ID NO 56
<211> LENGTH: 22
<212> TYPE: PRT
<213> ORGANISM: Artificial
<220> FEATURE:
<223> OTHER INFORMATION: synthetic GDF-9 analog

<400> SEQUENCE: 56

Leu Ser Val Leu Thr Ile Glu Pro Asp Gly Ser Ile Ala Tyr Lys Glu
1               5                   10                  15

Tyr Glu Asp Met Ile Ala
            20
```

-continued

<210> SEQ ID NO 57
<211> LENGTH: 15
<212> TYPE: PRT
<213> ORGANISM: Artificial
<220> FEATURE:
<223> OTHER INFORMATION: synthetic reverse BMP-2 analog

<400> SEQUENCE: 57

Leu Val Val Lys Glu Asn Glu Asp Leu Tyr Leu Met Ser Ile Ala
1 5 10 15

<210> SEQ ID NO 58
<211> LENGTH: 17
<212> TYPE: PRT
<213> ORGANISM: Artificial
<220> FEATURE:
<223> OTHER INFORMATION: synthetic reverse BMP-2 analog

<400> SEQUENCE: 58

Tyr Asn Lys Leu Val Val Lys Glu Asn Glu Asp Leu Tyr Leu Met Ser
1 5 10 15

Ile

<210> SEQ ID NO 59
<211> LENGTH: 13
<212> TYPE: PRT
<213> ORGANISM: Artificial
<220> FEATURE:
<223> OTHER INFORMATION: synthetic reverse BMP-7 analog

<400> SEQUENCE: 59

Lys Lys Leu Ile Val Asn Ser Ser Glu Asp Phe Tyr Leu
1 5 10

<210> SEQ ID NO 60
<211> LENGTH: 13
<212> TYPE: PRT
<213> ORGANISM: Artificial
<220> FEATURE:
<223> OTHER INFORMATION: synthetic reverse BMP-2 analog

<400> SEQUENCE: 60

Trp Asp Asn Trp Gly Val Asp Ser Phe Asp Val Tyr Leu
1 5 10

<210> SEQ ID NO 61
<211> LENGTH: 15
<212> TYPE: PRT
<213> ORGANISM: Artificial
<220> FEATURE:
<223> OTHER INFORMATION: synthetic reverse BMP-2 analog

<400> SEQUENCE: 61

Gly Glu Val Val Met Asp Gln Tyr Asn Lys Leu Val Val Lys Glu
1 5 10 15

<210> SEQ ID NO 62
<211> LENGTH: 16
<212> TYPE: PRT
<213> ORGANISM: Artificial
<220> FEATURE:
<223> OTHER INFORMATION: synthetic reverse BMP-2 analog

<400> SEQUENCE: 62

Leu His Asp Ala Leu Pro Phe Pro Cys Glu Gly His Cys Tyr Phe Ala
1 5 10 15

-continued

<210> SEQ ID NO 63
<211> LENGTH: 23
<212> TYPE: PRT
<213> ORGANISM: Artificial
<220> FEATURE:
<223> OTHER INFORMATION: synthetic reverse BMP-2 analog

<400> SEQUENCE: 63

```
Val Ser Asn Val Leu Thr Gln Val Ile Ala His Asn Thr Ser Asn Leu
1               5                   10                  15

His Asp Ala Leu Pro Phe Pro
            20
```

<210> SEQ ID NO 64
<211> LENGTH: 16
<212> TYPE: PRT
<213> ORGANISM: Artificial
<220> FEATURE:
<223> OTHER INFORMATION: synthetic reverse BMP-2 analog

<400> SEQUENCE: 64

```
Leu Val Val Lys Glu Asn Glu Asp Leu Tyr Leu Met Ser Ile Ala Cys
1               5                   10                  15
```

<210> SEQ ID NO 65
<211> LENGTH: 15
<212> TYPE: PRT
<213> ORGANISM: Artificial
<220> FEATURE:
<223> OTHER INFORMATION: synthetic HBGF analog

<400> SEQUENCE: 65

```
Arg Lys Leu Ala Val Tyr Trp Ser Ser Tyr Lys Arg Ser Arg Tyr
1               5                   10                  15
```

DUAL CHAIN SYNTHETIC HEPARIN-BINDING GROWTH FACTOR ANALOGS

CROSS-REFERENCE TO RELATED APPLICATIONS

This application is a continuation-in-part of U.S. patent application Ser. No. 11/064,039, entitled *Positive Modulator of Bone Morphogenic Protein*-2, filed on Feb. 22, 2005, now U.S. Pat. No. 7,482,427 which claims the benefit of the filing of U.S. Provisional Patent Application Ser. No. 60/547,012, entitled *Positive Modulator of Bone Morphogenic Protein*-2, filed on Feb. 20, 2004, and which is also a continuation-in-part application of U.S. patent application No. 10/644,703, entitled *Synthetic Heparin-Binding Growth Factor Analogs*, filed on Aug. 19, 2003, which in turn is a continuation-in-part application of U.S. patent application Ser. No. 10/224,268, entitled *Synthetic Heparin-Binding Growth Factor Analogs*, filed on Aug. 20, 2002, and the specification thereof of each is incorporated herein by reference.

This application claims the benefit of the filing of U.S. Provisional Patent Application Ser. No. 60/547,626, entitled *Dual Chain Synthetic Heparin-Binding Growth Factor Analogs*, filed on Feb. 24, 2004, and the specification thereof is incorporated herein by reference.

STATEMENT REGARDING FEDERALLY SPONSORED RESEARCH OR DEVELOPMENT

This invention was made with United States Government support under contract number DE-AC02-98CH10886, awarded by the U.S. Department of Energy. The United States Government has certain rights in the invention.

FIELD OF THE INVENTION

The invention relates to the field of synthetic peptides and analogs of heparin-binding growth factors, particularly analogs further having a non-growth factor heparin-binding region and optionally a linker, which linker may be hydrophobic. The invention further relates to the clinical uses of such analogs as soluble drugs and as coatings for medical devices.

BACKGROUND

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

The heparin-binding growth factors (HBGFs) constitute a large class of growth factors that includes the 23 fibroblast growth factors identified to date (FGFs 1-23), HBBM (heparin-binding brain mitogen), HB-GAF (heparin-binding growth associated factor), HB-EGF (heparin-binding EGF-like factor) HB-GAM (heparin-binding growth associated molecule), TGF-α (transforming growth factor-α), TGF-βs (transforming growth factor-βs), PDGF (platelet-derived growth factor), EGF (epidermal growth factor), VEGF (vascular endothelial growth factor), IGF-1 (insulin-like growth factor-1), IGF-2 (insulin-like growth factor-2), HGF (hepatocyte growth factor), IL-1 (interleukin-1), IL-2 (interleukin-2), IFN-α (interferon-α), IFN-γ (interferon-γ), TNF-α (tumor necrosis factor-α), SDGF (Schwannoma-derived growth factor) and the many other growth factors, cytokines, lymphokines and chemokines that have an affinity for heparin.

Peptides from natural HBGFs that bind heparin-binding growth factor receptors have been identified. See for example Ray et al., Proc. Natl. Acad. Sci. USA 94:7047-7052 (1997). These authors demonstrated that two amino acid sequences from FGF-2 are sufficient to block the mitogenic activity of FGF-2 on neural progenitor cells. The first peptide is a ten amino acid sequence, from amino acids 65-74, the second peptide extends from amino acids 115-129.

In an alternative approach, an artificial peptide that binds a heparin-binding growth factor receptor was identified by a phage display method. Ballinger et al., Nature BioTechnology 17:1199-1204 (1999) used this technique to isolate a 28 amino acid peptide called C19, binds FGF-2 receptors, but by itself fails to stimulate biological activity. The peptide has no amino acid sequence identity with any known FGF.

HBGFs useful in prevention or therapy of a wide range of diseases and disorders may be purified from natural sources or produced by recombinant DNA methods, however, such preparations are expensive and generally difficult to prepare.

Some efforts have been made to generate heparin-binding growth factor analogs. For example, natural PDGF occurs as an A chain and a B chain arranged in head-to-head (AA or BB) homodimers, or (AB or BA) heterodimers. Thus, U.S. Pat. No. 6,350,731 to Jehanli et al. discloses PDGF analogs in which two synthetic PDGF receptor-binding domains are covalently linked through a polyglycine or an N-(4-carboxy-cyclohexylmethyl)-maleimide (SMCC) chain to mimic the natural active polypeptide dimer.

U.S. Pat. No. 6,235,716 to Ben-Sasson discloses analogs of angiogenic factors. The analogs are branched multivalent ligands that include two or more angiogenic homology regions connected by a multilinker backbone.

U.S. Pat. No. 5,770,704 (the '704 patent) to Godowski discloses conjugates for activating receptor tyrosine kinases, cytokine receptors and members of the nerve growth factor receptor superfamily. The conjugates include at least two ligands capable of binding to the cognate receptor, so that the binding of the respective ligands induces oligomerization of these receptors. The ligands disclosed in the '704 patent are linked by covalent attachment to various nonproteinaceous polymers, particularly hydrophilic polymers, such as polyvinylalcohol and polyvinylpyrrolidone, and the polyvinylalkene ethers, including polyethylene glycol and polypropylene glycol. The ligands include hepatocyte growth factor (HGF) peptide variants that each bind HGF receptor, thereby causing receptor dimerization and activation of the biological activity of the HGF receptor dimer.

U.S. Pat. No. 6,284,503 (the '503 patent) to Caldwell et al. discloses a composition and method for regulating the adhesion of cells and biomolecules to hydrophobic surfaces and hydrophobic coated surfaces for cell adhesion, cell growth, cell sorting and biological assays. The composition is a biomolecule conjugated to a reactive end group activated polymer. The end group activated polymer includes a block copolymer surfactant backbone and an activation or reactive group. The block copolymer may be any surfactant having a hydrophobic region capable of adsorbing onto a hydrophobic surface, and a hydrophilic region which extends away from the surface when the hydrophobic region is adsorbed onto the hydrophobic surface. The '503 patent discloses that the biomolecules that may be conjugated to the end group activated polymer include natural or recombinant growth factors, such as PDGF, EGF, TGFα, TGFβ, NGF, IGF-I, IGF-II, GH and GHRF, as well as multi-CSF (II-3), GM-CSF, G-CSF, and M-CSF.

Other workers have described compositions that include homologs and analogs of fibroblast growth factors (FGFs). See for example U.S. Pat. No. 5,679,673 to Lappi and Baird; U.S. Pat. No. 5,989,866 to Deisher et al. and U.S. Pat. No. 6,294,359 to Fiddes et al. These disclosures relate to FGF homologs or analogs that are either conjugated to a toxic moiety and are targeted to the FGF receptor-bearing cells; or are homologs or analogs that modulate the biological pathways through the signal transduced by the FGF receptor upon binding by the FGF homolog or analog.

A series of patent applications to Kochendoerfer et al. disclose polymer-modified proteins, including synthetic chemokines and erythropoiesis stimulating proteins. See, for example, International Publications WO 02/04105, WO 02/19963 and WO 02/20033. These include chemically ligated peptide segments of a polypeptide chain of a synthetic erythropoiesis protein, such that a polypeptide chain results, with a water soluble polymer attached at one or more glycosylation sites on the protein. These applications also disclose synthetic chemokines, which are also polymer modified, and are asserted to be antagonists. However, heparin-binding domains are not disclosed. Other erythropoietin mimetics are known, such as those disclosed in U.S. Pat. Nos. 5,773,569 and 5,830,851 to Wrighton et al.

International Publication WO 00/18921 to Ballinger and Kavanaugh discloses a composition consisting of fusion proteins having FGF receptor affinity linked to an "oligomerization domain", either directly or through a linking group. The oligomerization domain ranges in length from about 20 to 300 residues, and includes constructs such as transcription factors, Fc portions of IgG, leucine zippers and the like. The oligomerization domains disclosed are homodimeric domains, wherein a single FGF receptor affinity fusion protein is linked to a single domain, such as a leucine zipper, which in turn is linked to a similar molecule by means of cysteine residues at both the amino and carboxy termini of the leucine zippers, such that two parallel leucine zippers, each with a single FGF receptor affinity fusion protein, are cross-linked by means of disulfide bonds. It is also disclosed that fusion proteins may include a heparin-binding domain, such as the use of jun as a multimerization domain, which is asserted to be a heparin binding domain. Thus the compositions disclosed by Ballinger and Kavanaugh are all composed of a single receptor-binding sequence covalently attached to an oligomerization domain, whereby two or more similar oligomerization domains, each with a single receptor-binding sequence, are conjoined by means of either an association provided by the oligomerization domain, or alternatively, are chemically cross-linked to provide for the covalent bonding of the individual components.

The above described homologs, analogs, conjugates or ligands each include a receptor-binding domain. However, none of the disclosed compositions further include both a linker, providing for the linking of two receptor-binding domains to a dipeptide sequence, and further providing a single non-signaling peptide containing a heparin-binding domain. Moreover, none of these or other known heparin-binding growth factor analogs provide the advantages described herein below. There is still a need for new peptide analogs of HBGFs, particularly for those that function as agonists. In particular, there is still a need for cost-effective synthetic peptide agonists of heparin-binding growth factor receptors, particularly synthetic heparin-binding growth factor agonists useful for coating medical devices and as soluble biologics.

SUMMARY OF THE INVENTION

In one embodiment, the invention provides a HBGF analog of formula I:

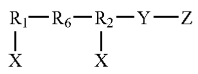

I wherein each X is a peptide chain that (i) has a minimum of three amino acid residues, (ii) has a maximum of about fifty amino acid residues, and (iii) binds a heparin-binding growth factor receptor (HBGFR); $R_1$ is an amino acid residue, wherein X is covalently bonded through the N-terminus of $R_1$ or through a side chain of $R_1$; $R_6$ is a linker comprising a chain from 3 to about 20 backbone atoms covalently bonded to $R_1$ and $R_2$; $R_2$ is a trifunctional alpha amino acid residue, wherein X is covalently bonded through a side chain of $R_2$; Y is a linker comprising a chain from 0 to about 50 backbone atoms covalently bonded to $R_2$ and Z; and Z is a non-signaling peptide chain that comprises a heparin binding domain, comprising an amino acid sequence that comprises (i) a minimum of one heparin binding motif, (ii) a maximum of about ten heparin binding motifs.

In the HBGF analog of formula I, $R_6$ can further include a linker that (i) comprises a chain of a minimum of about 3 and a maximum of about 20 atoms, and (ii) is not found in the natural ligand of the HBGFR which X binds. $R_6$ can further include a linker comprising a repeat unit, such as for example amino hexanoic acid (Hex) repeat units or amino acid repeat units, such as Gly repeats.

In the HBGF analog of formula I, Y can further include a linker that (i) is hydrophobic, (ii) comprises a chain of a minimum of about 9 and a maximum of about 50 atoms, and (iii) is not found in the natural ligand of the HBGFR which X binds. In one embodiment of formula I, $R_1$ is a trifunctional amino acid residue, wherein X is covalently bonded through a side chain of $R_1$.

In one embodiment of formula I, the HBGF analog of formula I is characterized in that it has an avidity for heparin such that the it binds heparin in 0.15 M NaCl, but is eluted by 1 M NaCl.

In another embodiment, the invention provides an HBGF analog of formula II:

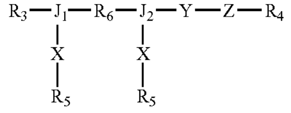

II wherein $R_3$ and $R_5$ are each independently $NH_2$, an acyl group with a linear or branched $C_1$ to $C_{17}$ alkyl, aryl, heteroaryl, alkene, alkenyl or aralkyl chain including a N-terminus $NH_2$, $NH_3^+$, or NH group or a corresponding acylated derivative, or is an amino acid, a dipeptide or a tripeptide, with an N-terminus $NH_2$, $NH_3^+$, NH group or a corresponding acylated derivative; $R_4$ is —OH, $NH_2$, NH—$R_7$, or is an amino acid, a dipeptide or a tripeptide with a C-terminus —OH, $NH_2$, or NH—$R_7$; $R_7$ is an aliphatic $C_1$ to $C_{17}$ chain; each X is a peptide chain that (i) has a minimum of three amino acid residues, (ii) has a maximum of about fifty amino acid residues, and (iii) binds a HBGFR; $J_1$ and $J_2$ are each independently a trifunctional alpha amino acid residue, wherein each X is covalently bonded through a side chain of $J_1$ or $J_2$; $R_6$ is a linker comprising a chain from 3 to about 20 backbone atoms covalently bonded to $J_1$ and $J_2$; Y is a linker comprising a chain from 0 to about 50 backbone atoms covalently bonded to $J_2$ and Z; and Z is a non-signaling peptide that comprises a heparin binding domain, comprising an amino acid sequence that comprises (i) a minimum of one heparin binding motif, (ii) a maximum of about ten heparin binding motifs, and (iii) a maximum of about thirty amino acids.

In the HBGF analog of formula II, $R_6$ can further include a linker that (i) comprises a chain of a minimum of about 1 and a maximum of about 20 atoms, and (ii) is not found in the natural ligand of the HBGFR which X binds. $R_6$ can further include a linker comprising a repeat unit, such as for example Hex repeat units or amino acid repeat units, such as Gly repeats.

In the HGBF analog of formula II, Y can further include a linker that (i) hydrophobic, (ii) comprises a chain of a minimum of about 9 and a maximum of about 50 atoms, and (iii) is not found in the natural ligand of the HBGFR which X binds.

In one embodiment, the HBGF analog of formula II is characterized in that it has an avidity for heparin such that it binds heparin in 0.15 M NaCl, but is eluted by 1 M NaCl.

The HBGF analog of formula II can further be characterized in that binding of it to the HBGFR initiates a signal by the HBGFR, or alternatively in that it blocks signaling by the HBGFR.

In one embodiment of the HBGF analog of formula II, $J_1$ and, if n=1, $J_2$, is a diamine amino acid residue. Such diamine amino acid residue may be a 2,3 diamino propionyl amino acid residue, a 2,4 diamino butylic amino acid residue, a lysyl residue or an ornithinyl residue. In an alternative embodiment of the HBGF analog of formula II, the side chain of $J_1$ and, if n=1, $J_2$, includes a reactive carboxyl group.

In one embodiment of the HBGF analog of formula II, the covalent bond between X and $J_1$ or, if n=1, $J_2$, comprises an amide, disulfide, thioether, Schiff base, reduced Schiff base, imide, secondary amine, carbonyl, urea, hydrazone or oxime bond. In a preferred embodiment, the bond is an amide bond.

The HBGF analog of formula II thus further includes a HBGF analog of formula III:

cyclized. Such cross-linking or cyclization may be through a covalent bond, including at least one disulfide, peptide, amide or thioether bond. In another embodiment, the terminal amines of each X, if provided, are crosslinked by means of a dialdehyde or by conjugation with a bifunctional crosslinking agent containing maleimides, aldehydes, succinymidal esters, benzotriazole carbonate, para-nitrophenol, or the like.

In another embodiment, in the HBGF analog of any of formula I or II, Y includes between one and about thirty-three ethylene glycol (oxyethylene) units. Alternatively, Y may include a branched or unbranched, saturated or unsaturated alkyl chain of between one and about twenty carbon atoms. In a particularly preferred embodiment, Y is $[NH_2—(CH_2)_p CO]_q$ wherein p is from 1 to about 10 and q is from 1 to about 20. In another embodiment, Y includes a peptide sequence, and in a preferred embodiment, with from one to about 16 Gly residues.

In another embodiment of the HBGF analog of any of formula I, II or III, each heparin binding motif of Z is BxBB, or BBBxxB, wherein each B independently represents lysine, arginine, ornithine, or histidine, and x represents a naturally occurring amino acid. In a preferred embodiment, Z includes at least two heparin-binding motifs, more preferably at least five heparin-binding motifs.

The present invention further includes a pharmaceutical composition including the HBGF analog of any of formula I, II or III, or a pharmaceutically acceptable salt thereof, and a pharmaceutical carrier.

The present invention further provides a method for treating a mammal that has been exposed to a harmful dose of radiation or a chemotherapeutic agent, the method comprising administering to the mammal an effective dose of a HBGF analog of any of formula I, II or III. Particularly preferred are HBGF wherein X binds an FGF HBGFR, and more preferably an FGF-7 receptor. The method includes administering to the mammal an effective dose of the synthetic heparin-binding growth factor analog to ameliorate the harmful effects of the radiation or chemotherapeutic agent, which may include mucositis, G.I. syndrome, or radionecrosis.

The present invention also provides a method for delivering an active peptide to a mammal, particularly a human. The method includes providing a medical device coated on the surface thereof via non-covalent bonds with a HBGF analog of any of formula I, II or III and placing the medical device onto a surface of, or implanting the medical device into, the mammal.

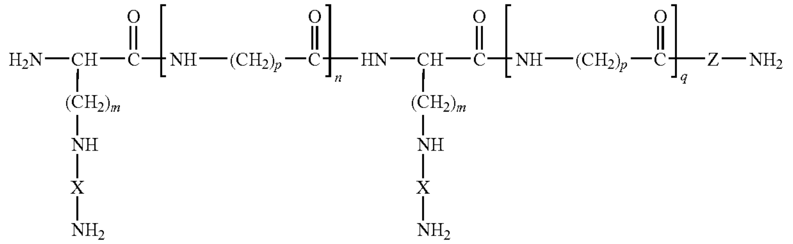

III wherein each m is independently from 1 to about 10, each p is independently from 1 to about 10, q is from 1 to about 20, and n is from 1 to about 6. In one particularly preferred embodiment, p is 5, q is 3, m is 4, and n is 3.

In one embodiment, in the HBGF analog of any of formulas I, II or III, the peptide chains X are cross-linked or Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Each synthetic HBGF analog of the invention is an analog of a particular HBGF that binds to one or more of the receptors bound by the particular HBGF. The synthetic HBGF analog may be an analog of a hormone, a cytokine, a lymphokine, a chemokine or an interleukin.

In one aspect the synthetic HBGF analog of the present invention is a molecule of any of formulas I, II, or III. HBGFs include any growth factor that binds selectively to heparin. For example, the HBGF can be any of the known FGFs (FGF-1 to FGF-23), HBBM (heparin-binding brain mitogen), HB-GAF (heparin-binding growth associated factor), HB-EGF (heparin-binding EGF-like factor) HB-GAM (heparin-binding growth associated molecule, also known as pleiotrophin, PTN, HARP), TGF-α (transforming growth factor-α), TGF-βs (transforming growth factor-βs), VEGF (vascular endothelial growth factor), EGF (epidermal growth factor), IGF-1 (insulin-like growth factor-1), IGF-2 (insulin-like growth factor-2), PDGF (platelet derived growth factor), RANTES, SDF-1, secreted frizzled-related protein-1 (SFRP-1), small inducible cytokine A3 (SCYA3), inducible cytokine subfamily A member 20 (SCYA20), inducible cytokine subfamily B member 14 (SCYB14), inducible cytokine subfamily D member 1 (SCYD1), stromal cell-derived factor-1 (SDF-1), thrombospondins 1, 2, 3 and 4 (THBS1-4), platelet factor 4 (PF4), lens epithelium-derived growth factor (LEDGF), midikine (MK), macrophage inflammatory protein (MIP-1), moesin (MSN), hepatocyte growth factor (HGF, also called SF), placental growth factor, IL-1 (interleukin-1), IL-2 (interleukin-2), IL-3 (interleukin-3), IL-6 (interleukin-6), IL-7 (interleukin-7), IL-10 (interleukin-10), IL-12 (interleukin-12), IFN-α (interferon-α), IFN-γ (interferon-γ), TNF-α (tumor necrosis factor-α), SDGF (Schwannoma-derived growth factor), nerve growth factor, neurite growth-promoting factor 2 (NEGF2), neurotrophin, BMP-2 (bone morphogenic protein 2), OP-1 (osteogenic protein 1, also called BMP-7), keratinocyte growth factor (KGF), interferon-γ inducible protein-20, RANTES, and HIV-tat-transactivating factor, amphiregulin (AREG), angio-associated migratory cell protein (AAMP), angiostatin, betacellulin (BTC), connective tissue growth factor (CTGF), cysteine-rich angiogenic inducer 61 (CYCR61), endostatin, fractalkine/neuroactin, or glial derived neurotrophic factor (GDNF), GRO2, hepatoma-derived growth factor (HDGF), granulocyte-macrophage colony stimulating factor (GMCSF), and the many growth factors, cytokines, interleukins and chemokines that have an affinity for heparin.

The amino acid sequences of many of these and other HBGFs are available from the National Library of Medicine Protein Database at the world wide web address ncbi.nlm.nih.gov/entrez. These HBGF amino acid sequences on the foregoing internet site are hereby incorporated by reference. The use of synthetic HBGF analogs incorporating the amino acid sequences of the receptor binding domains from these and other HBGFs is specifically contemplated in the present invention.

In particular embodiments of the present invention, the synthetic HBGF analog of the present invention consists essentially of the molecule of any one of formula I, II or III, i.e. the molecule of any one of formula I, II or III is the major active component in the synthetic HBGF analog composition.

In other particular embodiments, the synthetic HBGF analog of the present invention consists entirely of the molecule of any one of formula I, II or III, i.e. the molecule of any one of formula I, II or III is the only component in the synthetic HBGF analog composition.

As used here and elsewhere, the following terms have the meanings given.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical—$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C═O)—} groups. A peptide is most usually acylated at the N-terminus.

An "amide" includes compounds that have a trivalent nitrogen attached to a carbonyl group (—$CO.NH_2$).

An "amine" includes compounds that contain an amino group (—$NH_2$).

A "diamine amino acid" is an amino acid or residue containing two reactive amine groups and a reactive carboxyl group. Representative examples include 2,3 diamino propionyl amino acid, 2,4 diamino butylic amino acid, lysine or ornithine.

A "trifunctional amino acid" is an amino acid or residue with three reactive groups, one the N-terminus amine, a second the C-terminus carboxyl, and the third comprising all or a part of the side chain. Trifunctional amino acids thus include, by way of example only, diamine amino acids; amino acids with a reactive sulfhydryl group in the side chain, such as mercapto amino acids including cysteine, penicillamine, or 3-mercapto phenylalanine; amino acids with a reactive carboxyl group in the side chain, such as aspartic acid and glutamic acid; and amino acids with a reactive guanadium group in the side chain, such as arginine.

The Heparin-Binding Growth Factors of Formulas I to III

The regions X and Z of the synthetic HBGF analogs of formulas I to III include amino acid residues, and optionally the regions $R_6$ and Y include amino acid residues. An amino acid residue is defined as —NHRCO—, where R can be hydrogen or any organic group. The amino acids can be D-amino acids or L-amino acids. Additionally, the amino acids can be α-amino acids, β-amino acids, γ-amino acids, or δ-amino acids and so on, depending on the length of the carbon chain of the amino acid.

The amino acids of the X, $R_6$, Y and Z component regions of the synthetic HBGF analogs of the invention can include any of the twenty amino acids found naturally in proteins, i.e. alanine (ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine, (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, $R_6$, Y and Z component regions of the synthetic HBGF analogs of the invention can include any of the naturally occurring amino acids not found naturally in proteins, e.g. β-alanine, betaine (N,N, N-trimethylglycine), homoserine, homocysteine, γ-amino butyric acid, ornithine, citrulline and the like.

Additionally, the amino acids of the X, $R^6$, Y and Z component regions of the synthetic HBGF analogs of the invention can include any of the non-biological amino acids, i.e. those not normally found in living systems, such as for instance, a straight chain amino-carboxylic acid not found in nature. Examples of straight chain amino-carboxylic acids not found in nature include 6-aminohexanoic acid, 7-aminoheptanoic acid, 9-aminononanoic acid and the like.

In formula I, one X region is covalently linked through an amino acid $R_1$, which is in turn covalently linked to a linker group $R_6$, which is linked to a second amino acid, $R_2$, which is a trifunctional alpha amino acid, and preferably a diamine amino acid. The second X region is covalently linked to $R_2$ through a second reactive group of $R_2$, such as the second amino group of a diamine amino acid. $R_2$ is then covalently linked through its carboxy terminus to the Y region of the synthetic HBGF analog. Similarly, in formula II one X region is covalently linked through a reactive side chain of an amino acid $J_1$, which is in turn covalently linked to $R_6$ which is linked to a second amino acid, $J_2$, both $J_1$ and $J_2$ constituting trifunctional amino acids, preferably diamine amino acids. The second X region is covalently linked to $J_2$ through a second reactive group of $J_2$, such as the second amino group of a diamine amino acid. $J_2$ is then covalently linked through its carboxy terminus to the Y region of the synthetic HBGF analog.

The amino acid $R_1$ of formula I can be any of the amino acids described above. $R_2$ of formula I, and $J_1$ and $J_2$ of formula II, can be any trifunctional amino acid residue, preferably a trifunctional alpha amino acid residue. In a preferred embodiment, the trifunctional amino acid residue is a diamine amino acid, such as for instance lysine or ornithine, or any other amino acid having two amino groups.

The region X of formulas I to III of the synthetic HBGF analogs of the present invention is a synthetic peptide chain that binds an HBGFR. Region X can, for example, have any amino acid sequence that binds an HBGFR, and can include amino acid sequences that are identical to a portion of the amino acid sequence of a HBGF. Alternatively, X can have an amino acid sequence homologous rather than identical to the amino acid sequence of an HBGF. The particular HBGFR bound by the synthetic HBGF analog of the invention may or may not be the cognate receptor of the original HBGF, i.e. the synthetic HBGF analog may additionally or solely bind to the receptor of a different HBGF.

The term "homologous", as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20% or 25% of the amino acid residues when the amino acid sequences of the two peptide homologs are aligned.

Particularly useful amino acid sequences as X regions of formulas I to III include homologs of fragments of naturally occurring HBGFs that differ from the amino acid sequences of natural growth factor in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another of the same acidic or basic character or the replacement of cysteine with serine.

In another alternative, the X region of the synthetic HBGF analog can include an amino acid sequence that shows no detectable homology to the amino acid sequence of any HBGF. Peptides or growth factor analogs useful as components of the X region of the synthetic analogs of the present invention, that have little or no amino acid sequence homology with the cognate growth factor and yet bind HBGFRs may be obtained by any of a wide range of methods, including for instance, selection by phage display. See as an example: Sidhu et al. Phage display for selection of novel binding peptides. *Methods Enzymol.* 328:333-63 (2000).

The X region of the synthetic HBGF analogs of the invention can have any length that includes an amino acid sequence that effectively binds an HBGFR. Preferably, the X regions of the synthetic HBGF analogs have a minimum length of at least approximately three amino acid residues. More preferably, the X regions of the synthetic HBGF analogs have a minimum length of at least approximately six amino acid residues. Most preferably the X regions of the synthetic HBGF analogs have a minimum length of at least approximately ten amino acid residues. The X regions of the synthetic HBGF analogs of the invention preferably also have a maximum length of up to approximately fifty amino acid residues, more preferably a maximum length of up to approximately forty amino acid residues, and most preferably a maximum length of up to approximately thirty amino acid residues.

In one embodiment of the synthetic HBGF analogs that include two X regions, the X regions are covalently cross-linked. Suitable cross-links can be formed by S—S bridges of cysteines linking the two X regions. Alternatively, the cross link can be conveniently formed during simultaneous and parallel peptide synthesis of the X region amino acids chains by incorporating a lanthionine (thio-dialanine) residue to link the two identical X chains at alanine residues that are covalently bonded together by a thioether bond. In another method the two X region amino acid chains can be cross-linked by introducing a cross-linking agent, such as a dicarboxylic acid, e.g. suberic acid (octanedioic acid), or the like, thereby introducing a hydrocarbon bridge between the two identical X regions having a free amino, hydroxyl or thiol group. The cross-linked X regions can constitute a cyclic peptide, such as where the terminal amino acids of X are cross-linked through reactive side chains or the terminal groups, optionally with a bridge or other link. In the case of the thiol groups, the bridge can be formed directly by the formation of a disulfide bond, or alternatively by the use of a bifunctional, thiol-reactive cross-linking agent containing, for example, the thiol-reactive maleimide group(s). In the case of amino groups, the amino groups can be cross-linked by the use of a bifunctional crosslinking agent containing two aldehyde groups, such as glutaraldehyde or propionaldehyde. The amines may also be crosslinked by any number of crosslinking agents known to those skilled in the art, such as those containing, for example, succinylmidal esters, benzotriazole carbonate or paranitrophenol.

The $R_6$ region of formulas I and II can include a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids).

The chain of atoms of the $R_6$ region of formula I is covalently attached to $R_1$ and $R_2$. Similarly the chain of atoms of the $R_6$ region of formula II is covalently attached to $J_1$ and $J_2$. The covalent bonds can be, for example, peptide, amide or ester bonds. Preferably, the $R_6$ region includes a chain of a minimum of about one atom. More preferably, the $R_6$ region includes a chain of a minimum of about three atoms. For example, the $R_6$ region may be formed from a chain of at least one, at least two or at least three amino acids. Alternatively, the $R_6$ region may be formed from a chain of at least one, at least two, or at least three aminohexanoic acid residues.

Preferably, the $R_6$ region includes a chain of a maximum of about twenty atoms. The amino acid sequence of the $R_6$ region of formula I or II is preferably an artificial sequence, i.e. it does not include any amino acid sequence of four or more amino acid residues found in a natural ligand of a HBGF.

In a particular embodiment, the $R_6$ region includes a hydrophobic amino acid residue, or a chain of hydrophobic amino acid residues. The $R_6$ region can, for example, include one or more aminohexanoic acid residues, such as one, two, three or more aminohexanoic acid residues.

In another particular embodiment, the $R_6$ region of the molecule of formula I or II can include a branched or unbranched, saturated or unsaturated alkyl chain of between one and about twenty carbon atoms. In a further embodiment, the $R_6$ region can include a chain of hydrophobic residues, such as for instance, ethylene glycol residues. For instance, the $R_6$ region can include at least about three, or at least about four, or at least about five ethylene glycol residues. Alternatively, the $R_6$ region can include up to about twelve, up to about fifteen, or up to about seventeen ethylene glycol residues. In another alternative embodiment, the $R_6$ region can include a combination of amino acid hydrophobic residues.

In the synthetic HBGF analogs of the present invention, in one preferred embodiment the Y region of formulas I to III is a linker that is sufficiently hydrophobic to non-covalently bind the HBGF analog to a polystyrene or polycaprolactone surface, or the like. In addition, the Y region may bind to other hydrophobic surfaces, particularly the hydrophobic surfaces formed from materials used in medical devices. Such surfaces are typically hydrophobic surfaces. Examples of suitable surfaces include but are not limited to those formed from hydrophobic polymers such as polycarbonate, polyester, polypropylene, polyethylene, polystyrene, polytetrafluoroethylene, expanded polytetrafluoroethylene, polyvinyl chloride, polyamide, polyacrylate, polyurethane, polyvinyl alcohol, polyurethane, poly ethyl vinyl acetate, poly(butyl methacrylate), poly(ethylene-co-vinyl acetate), polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steel, titanium, platinum, and nitinol. Preferably, the binding of the HBGF analogs to the hydrophobic surface is of sufficient quantity to be detected by an analytical method such as an enzyme-linked immunoassay or a biological assay.

The Y region of formulas I to III can include a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids).

The chain of atoms of the Y region of formula I is covalently attached to $R_2$ and to peptide Z. Similarly the chain of atoms of the Y region of formula II is covalently attached to $J_2$ and to peptide Z. The covalent bonds can be, for example, peptide, amide or ester bonds. Preferably, the Y region includes a chain of a minimum of about nine atoms. More preferably, the Y region includes a chain of a minimum of about twelve atoms. Most preferably, the Y region includes a chain of a minimum of about fifteen atoms. For example, the Y region may be formed from a chain of at least four, at least five or at least six amino acids. Alternatively, the Y region may be formed from a chain of at least one, at least two, or at least three aminohexanoic acid residues.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For example, the Y region may be formed from a chain of up to about twelve, up to about fifteen, or up to about seventeen amino acids.

The amino acid sequence of the Y region of formula I or II is preferably an artificial sequence, i.e. it does not include any amino acid sequence of four or more amino acid residues found in a natural ligand of a HBGF.

In a particular embodiment, the Y region includes a hydrophobic amino acid residue, or a chain of hydrophobic amino acid residues. The Y region can, for example, include one or more aminohexanoic acid residues, such as one, two, three or more aminohexanoic acid residues.

In another particular embodiment, the Y region of the molecule of formula I or II can include a branched or unbranched, saturated or unsaturated alkyl chain of between one and about twenty carbon atoms. In a further embodiment, the Y region can include a chain of hydrophobic residues, such as for instance, ethylene glycol residues. For instance, the Y region can include at least about three, or at least about four, or at least about five ethylene glycol residues. Alternatively, the Y region can include up to about twelve, up to about fifteen, or up to about seventeen ethylene glycol residues. In another alternative embodiment, the Y region can include a combination of amino acid hydrophobic residues.

The Z region of the molecule of formula I to III is a heparin-binding region and can include one or more heparin-binding motifs, BBxB or BBBxxB as described by Verrecchio et al. J. Biol. Chem. 275:7701 (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR] (SEQ ID NO:1), designating the first three amino acids as each independently selected from lysine or arginine, followed by any two amino acids and a sixth amino acid which is lysine or arginine.

The number of heparin binding motifs is variable. For instance, the Z region may include at least one, at least two, at least three or at least five heparin-binding motifs. Where there are more than one heparin-binding motifs, the motifs may be the same or different. Alternatively, the Z region includes up to a maximum of about ten heparin-binding motifs. In another alternative embodiment, the Z region includes at least four, at least six or at least eight amino acid residues. Further, in certain embodiments the Z region includes up to about twenty, up to about, twenty-five, or up to about thirty amino acid residues. It is to be realized that, in part, the avidity of the Z region for heparin is determined by the particular heparin-binding motifs selected and the number of such motifs in Z. Thus for particular applications both the selection and number of such motifs may be varied to provide optimal heparin binding of the Z region.

In a preferred embodiment, the amino acid sequence of the Z region is RKRKLERIAR (SEQ ID NO:2). In another embodiment, the amino acid sequence of the Z region is RKRKLGRIAR (SEQ ID NO:3). In yet another embodiment, the amino acid sequence of the Z region is RKRKLWRARA (SEQ ID NO:4). In yet another embodiment, the amino acid sequence of the Z region is RKRLDRIAR (SEQ ID NO:5). In yet another embodiment, the amino acid sequence of the Z region is RKRKLERIARC (SEQ ID NO:6). The presence of a terminal cysteine residue optionally affords the opportunity to link other molecules, including detection reagents such as fluorochromes, radioisotopes and other detectable markers, to the Z region, as well as the opportunity to link toxins, immunogens and the like.

Heparin-binding domains that bear little or no sequence homology to known heparin-binding domains are also contemplated in the present invention. As used herein the term "heparin-binding" means binding to the —$NHSO_3^-$ and sulfate modified polysaccharide, heparin, and also binding to the related modified polysaccharide, heparan sulfate, as well as glycosaminoglycans or proteoglycans containing heparin or heparin sulfate, as well as degration products of the aforementioned, and synthetic polysaccharides that exhibit heparin-like activity.

The Z region of the synthetic HBGF analogs of the present invention confers the property of binding to heparin in low salt concentrations, up to about 0.15 M NaCl, optionally up to about 0.48 M NaCl, forming a complex between heparin and the Z region of the factor analog. The complex can be dissociated in 1 M NaCl to release the synthetic HBGF analog from the heparin complex.

The Z region is a non-signaling peptide relative to the HBGFR. Accordingly, when used alone the Z region binds to heparin which can be bound to a receptor of a HBGF, but the binding of the Z region peptide alone does not initiate or block signaling by the receptor.

The C-terminus of the Z region may be blocked or free. For example, the C terminus of the Z region may be the free carboxyl group of the terminal amino acid, or alternatively, the C terminus of the Z region may be a blocked carboxyl group, such as for instance, an amide group. In a preferred embodiment the C terminus of the Z region is an amidated arginine.

FGF Synthetic Analogs

In another particular aspect, the invention provides a synthetic FGF peptide analog. The synthetic FGF analogs represented by any of formulas of the present invention, wherein X is an FGF analog which can be any FGF, such as any of the known FGFs, including all 23 FGFs from FGF-1 to FGF-23.

The X region of the molecule of formulas of the present invention can include an amino acid sequences found in an FGF, such as for instance FGF-2 or FGF-7. Alternatively, the X regions can include sequences not found in the natural ligand of the FGFR bound by the molecule.

The Y region of the synthetic FGF peptide analogs of any of the formulas of the present invention are not necessarily hydrophobic, and thus, if present, can be polar, basic, acidic, hydrophilic or hydrophobic. Thus, the amino acid residues of the Y region of synthetic FGF peptide analogs can include any amino acid, or polar, ionic, hydrophobic or hydrophilic group.

The X region of synthetic FGF peptide analogs can include an amino acid sequence that is 100% identical to an amino acid sequence found in a fibroblast growth factor or an amino acid sequence homologous to the amino acid sequence of a fibroblast growth factor. For instance, the X region can include an amino acid sequence that is at least about 50%, at least about 75%, or at least about 90% homologous to an amino acid sequence from a fibroblast growth factor. The fibroblast growth factor can be any fibroblast growth factor, including any of the known or yet to be identified fibroblast growth factors.

In a particular embodiment, the synthetic FGF analog of the invention is an agonist of the HBGFR. When bound to the HBGFR, the synthetic HBGF analog initiates a signal by the HBGFR.

In a further particular embodiment, the synthetic FGF analog of the invention is an antagonist of the HBGFR. When bound to the HBGFR, the synthetic HBGF analog blocks signaling by the HBGFR.

In another particular embodiment of the present invention, the synthetic FGF analog is an analog of FGF-2 (also known as basic FGF, or bFGF). In another particular embodiment of the present invention, the binding of the synthetic FGF analog to an FGF receptor initiates a signal by the FGF receptor. In a further particular embodiment, the binding of the synthetic FGF analog to the FGF receptor blocks signaling by the FGF receptor.

In a yet further particular embodiment, the present invention provides a synthetic FGF analog of FGF-2. In another particular embodiment, the present invention provides a synthetic FGF analog of FGF-2, wherein the amino acid sequence of the X region is YRSRKYTSWYVALKR (SEQ ID NO:7) from FGF-2. In yet another particular embodiment, the present invention provides a synthetic FGF analog wherein the amino acid sequence of the X region is NRFHSWDCIKTWASDTFVLVCYDDGSEA (SEQ ID NO:8). In yet another particular embodiment, the present invention provides a synthetic FGF-2 analog wherein the amino acid sequence of the X region is HIKLQLQAEERGWS (SEQ ID NO:9).

In a yet further particular embodiment, the invention provides a synthetic FGF analog of FGF-1, wherein the X region is YISKKHAEKNWFVGLKK (SEQ ID NO:10). This sequence is derived from amino acids bridging the beta 9 and beta 10 loop of FGF-1. In yet another particular embodiment, an FGF-1 analog is provided wherein the X region is HIQLQLSAESVGEVY (SEQ ID NO:11), corresponding to amino acids derived from the β-4 and β-5 region of FGF-1.

In a yet further particular embodiment, the invention provides a synthetic FGF analog of FGF-7, wherein the X region is YASAKWTHNGGEMFVALNQK (SEQ ID NO:12). In yet another embodiment of a synthetic FGF analog of FGF-7, the X region is the amino acid sequence YNIMEIRTVAVGIVA (SEQ ID NO:13).

Other FGF receptor binding domains, derived largely from targeting sequences in the C-terminus of human FGF, include the following sequences shown in Table 1:

TABLE 1

| CYTOKINE | PREFERRED X RECEPTOR BINDING DOMAIN | |
|---|---|---|
| FGF-10 | YASFNWQHNGRQMYVALNQK | (SEQ ID NO:14) |
| FGF-22 | YASQRWRRRGQPNLALDRR | (SEQ ID NO:15) |
| FGF-9 | YSSNLYKHVDTGRRYYVALNK | (SEQ ID NO:16) |
| FGF-16 | YASTLYKHSDSERQYVALNK | (SEQ ID NO:17) |
| FGF-20 | YSSNIYKHGDTGRRFVALNK | (SEQ ID NO:18) |
| FGF-4 | YESYKYPGMFIALSKN | (SEQ ID NO:19) |
| FGF-6 | YESDLYQGTYILSKYGR | (SEQ ID NO:20) |
| FGF-12 | YSSTLYRQQESGRAWFLGNK | (SEQ ID NO:21) |
| FGF-14 | YSSMLYRQQESGRAWFLGLNK | (SEQ ID NO:22) |
| FGF-13 | YSSMIYRQQQSGRGWYLGLNK | (SEQ ID NO:23) |
| FGF-11 | YASALYRQRRSGRAWYLDK | (SEQ ID NO:24) |

VEGF Synthetic Analogs

In another particular aspect, the invention provides a synthetic VEGF peptide analog. The synthetic VEGF analogs represented include, in one embodiment, a VEGF analog wherein the amino acid sequence of the X region is APMAEGGGQNHHEVVKFMDV (SEQ ID NO:25). In another embodiment, there is provided a synthetic VEGF peptide analog wherein the amino acid sequence of the X region is GATWLPPNPTK (SEQ ID NO:26). In yet another embodiment, there is provided a synthetic VEGF peptide analog wherein the amino acid sequence of the X region is NFLLSWVHWSLALLLYLHHA (SEQ ID NO:27).

BMP Synthetic Analogs

In another particular aspect, the invention provides a synthetic BMP peptide analog. The synthetic bone morphogenic protein analogs include embodiments wherein the X region includes the amino acid sequence LYVDFSDVGWNDW (SEQ ID NO:28), AISMLYLDENEKVVL (SEQ ID NO:29), ISMLYLDENEKVVLKNY (SEQ ID NO:30), EKVVLKNYQDMVVEG (SEQ ID NO:31), LVVKENEDLYLMSIAC (SEQ ID NO:32), AFYCHGECPFPLADHL (SEQ ID NO:33), or PFPLADHLNSTNHAIVQTLVNSV (SEQ ID NO:34).

Alternatively, in another particular aspect the invention provides synthetic BMP, TGF or GDF (growth differentiation factor) peptide analogs as shown in Table 2 wherein the transforming growth factor family member peptides are particularly useful in augmenting the activity of endogenous or artificial BMP peptides or TGF peptides, wherein is shown (under the heading "preferred receptor binding domain") the sequence forming all or part of the X region of constructs of any of formulas I to III.

TABLE 2

| CYTOKINE | PREFERRED X RECEPTOR BINDING DOMAIN | |
|---|---|---|
| TGF-β1 | IVYYVGRKPKVEQLSNMIVRS | (SEQ ID NO:35) |
| TGF-β2 | TILYYIGKTPKIEQLSNMIVKS | (SEQ ID NO:36) |
| TGF-β3 | LTILYYVGRTPKVEQLSNMVV | (SEQ ID NO:37) |
| BMP-2 | AISMLYLDENEKVVLKNYQDMVV | (SEQ ID NO:38) |
| BMP-3 | SSLSILFFDENKNVVLKVYPNMTV | (SEQ ID NO:39) |
| BMP-3β | NSLGVLFLDENRNVVLKVYPNMSV | (SEQ ID NO:40) |
| BMP-4 | AISMLYLDEYDKVVLKNYQEMVV | (SEQ ID NO:41) |
| BMP-5 | AISVLYFDDSSNVILKKYRNMVV | (SEQ ID NO:42) |
| BMP-6 | AISVLYFDDNSNVILKKYRNMVV | (SEQ ID NO:43) |
| BMP-7 | AISVLYFDDSSNVILKKYRNMVV | (SEQ ID NO:44) |
| BMP-8 | ATSVLYYDSSNNVILRKARNMVV | (SEQ ID NO:45) |
| BMP-9 | ISVLYKDDMGVPTLKYHYEGMSV | (SEQ ID NO:46) |
| BMP-10 | ISILYLDKGVVTYKFKYEGMAV | (SEQ ID NO:47) |
| BMP-11 | INMLYFNDKQQIIYGKIPGMVV | (SEQ ID NO:48) |
| BMP-12 | ISILYIDAANNVVYKQYEDMVV | (SEQ ID NO:49) |
| BMP-13 | ISILYIDAGNNVVYKQYEDMVV | (SEQ ID NO:50) |
| BMP-14 | ISILFIDSANNVVYKQYEDMVV | (SEQ ID NO:51) |
| BMP-15 | ISVLMIEANGSILYKEYEGMIA | (SEQ ID NO:52) |
| GDF-1 | ISVLFFDNSDNVVLRQYEDMVV | (SEQ ID NO:53) |
| GDF-3 | ISMLYQDNNDNVILRHYEDMVV | (SEQ ID NO:54) |
| GDF-8 | INMYLFNGKEQIIYGKIPAMVV | (SEQ ID NO:55) |
| GDF-9 | LSVLTIEPDGSIAYKEYEDMIA | (SEQ ID NO:56) |

It has surprisingly and advantageously been found that in the compounds of the present invention, including those of formulas I to III, the X region may be synthesized in a reverse direction, such that considering the sequence AISMLYLDENEKVVL (SEQ ID NO:29) illustrated in the conventional N→C orientation, and using formula I, the first amino acid bound to either the $R_1$ side chain or N-terminus amine is the N-terminus amino acid residue (bound through its carboxyl group thereby forming a peptide bond), the second amino acid bound to the N-terminus amino acid residue is the 2 position residue, and so on, and the compounds nonetheless retain biological activity and specifically bind to a BMP receptor. It may be seen that such a construct has, based on a conventional N→C orientation, a reverse sequence, in that it is the carboxyl group of the conventional N-terminus amino acid residue that forms a peptide bond with an amine of $R_1$ where $R_1$ is a diamine amino acid. Thus again employing a conventional N→C orientation, the foregoing sequences may be employed in a reverse orientation, and the resulting compound of present invention is biologically active and may be employed as described herein. According to a preferred embodiment, the X region is the sequence LVVKENED- LYLMSIA (SEQ ID NO:57) (again considering the sequence in the conventional N→C orientation.

Other reverse sequences that may be employed, in whole or in part, including homologs thereto, in addition to LVVKENEDLYLMSIA (SEQ ID NO:57), include but are not limited to YNKLVVKENEDLYLMSI (SEQ ID NO:58), KKLIVNSSEDFYL (SEQ ID NO:59), WDNWGVDSFD-VYL (SEQ ID NO:60), GEVVMDQYNKLVVKE (SEQ ID NO:61), LHDALPFPCEGHCYFA (SEQ ID NO:62), VSN-VLTQVIAHNTSNLHDALPFP (SEQ ID NO:63), and LVVKENEDLYLMSIAC (SEQ ID NO:64).

Methods of Synthesizing the Heparin-Binding Growth Factor Analogs

The synthesis of the analogs of the invention can be achieved by any of a variety of chemical methods well known in the art. Such methods include bench scale solid phase synthesis and automated peptide synthesis in any one of the many commercially available peptide synthesizers. Preferably, the synthesizer has a per-cycle coupling efficiency of greater than 99 percent. Such methods may also include liquid phase synthesis, or a combination of solid phase and liquid synthesis.

The analogs of the present invention can be produced by stepwise synthesis or by synthesis of a series of fragments that can be coupled by similar well-known techniques. See, for instance, Nyfeler, Peptide synthesis via fragment condensation. *Methods Mol Biol* 35:303-16 (1994); and Merrifield, Concept and early development of solid-phase peptide synthesis. *Methods in Enzymol* 289:3-13 (1997). These methods are routinely used for the preparation of individual peptides. It is possible to assemble the analogs of the present invention in component parts, such as peptides constituting the X, $R_6$, Y and Z components thereof, and to thereafter couple such component parts to assemble the analog. See, for instance, Dawson and Kent, Synthesis of native proteins by chemical ligation. *Annu. Rev. Biochem.* 69:923-960 (2000); and Eorn et al., Tandem ligation of multipartite peptides with cell-permeable activity. *J. Am. Chem. Soc.* 125:73-82 2003).

Advantageously, in the case where the analogs of formulas I to III of the invention include two identical X region amino acid sequences, the synthesis of these identical X region peptides may be performed in parallel. By this method each cycle of addition adds an amino acid to both of the X region peptides, greatly facilitating the synthesis of these branched molecules.

Peptide libraries that can be used to screen for a desired property, such as binding to an HBGFR can be prepared by adaptations of these methods. See for instance, Fox, Multiple peptide synthesis, *Mol. Biotechnol.* 3:249-58 (1995); and Wade and Tregear, Solid phase peptide synthesis: recent advances and applications. *Austral. Biotechnol.* 3:332-6 (1993).

In a particular embodiment, the synthetic HBGF analog of the invention is an agonist of the HBGFR. When bound to the HBGFR, the synthetic HBGF analog initiates a signal by the HBGFR.

In another particular embodiment, the synthetic HBGF analog of the invention is an antagonist of the HBGFR. When bound to the HBGFR, the synthetic HBGF analog blocks signaling by the HBGFR.

In a particular aspect, the invention provides a method for stimulating growth factor receptor signaling in a cell by contacting the cell with an effective amount of a synthetic HBGF analog according to formulas I to III. The effective amount can be readily determined by one of skill in the art. The signaling can result in cytokine release from the cell, stimulation or inhibition of proliferation or differentiation of the cell, chemotaxis of the cell, stimulation or inhibition of the immune system of the mammal.

Methods of Use of the HBGFs of the Invention

The HBGF analogs of the invention provide a cost effective and potentially unlimited source of biologically active molecules that are useful in a number of ways, including as soluble prophylactic or therapeutic pharmaceutical agents, such as for instance for administration as a soluble drug for prevention or treatment of various diseases, including for example, uses in cancer therapy and radioprotection.

The synthetic HBGF analogs of present invention are also useful as biologically active agents for coating of medical devices, such as for instance, sutures, implants and medical instruments to promote biological responses, for instance, to stimulate growth and proliferation of cells, or healing of wounds.

In one aspect, the present invention provides a method for treating a mammal that has been exposed to a harmful dose of radiation. The method includes administering an effective dose of a synthetic HBGF analog of the invention which is an FGF analog to the mammal. The treatment is particularly useful in the prevention or treatment of mucositis, gastrointestinal syndrome (G.I. syndrome), or radionecrosis such as can result from exposure to radiation. The HBGF analog can be administered parenterally, orally, or topically. Alternatively, the HBGF analog can be delivered loco-regionally, e.g. on an analog coated medical device. In a related embodiment, the present invention provides a method for treating a mammal that has been administered a dose of a chemotherapeutic agent, to ameliorate the toxicity of the chemotherapeutic agent to the mammal. In a particular embodiment of the above-described methods, the mammal is a human. In another particular embodiment of the method, the HBGF analog is an FGF-2 analog or an FGF-7 analog.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, aneurysm coils, embolization particles, microbeads, dental implants, bone prostheses, tissue scaffolds, artificial joints or a controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al. in U.S. Pat. No. 6,342,591 teach an amphipathic coating for medical devices for modulating cellular adhesion composition, and is incorporated herein by reference.

In one embodiment the invention provides a method for delivering an active peptide to a mammal, the method includes (i) providing a medical device coated on its surface with a synthetic HBGF analog of formulas I to III, the synthetic HBGF analog being bound to the surface of the medical device by non-covalent bonds; and (ii) placing the medical device onto a surface of, or implanting the medical device into, the mammal.

In a particular embodiment of the above method, the non-covalent bonds are associations between the heparin binding domain of the synthetic HBGF analog and a heparin-containing compound bound to the surface of the medical device. The heparin-containing compound bound to the surface of the medical device can be any heparin-containing compound, such as for instance, benzyl-bis(dimethylsilylmethyl)oxy carbamoyl-heparin.

In another particular embodiment of the above method, the medical device is not pre-coated with a heparin-containing compound before being coated with the synthetic HBGF analog of formulas I to III Heparin-Binding Growth Factors The fibroblast growth factors, FGFs, constitute a family of related proteins controlling normal growth and differentiation of mesenchymal, epithelial, and neuroectodermal cell types. Homologs have been found in a wide variety of species. FGFs show a very high affinity to heparin and are therefore also referred to as heparin-binding growth factors (HBGFs). As used herein, the term HBGFs includes all FGFs.

Two main types of FGF are known. The first type of FGF was isolated initially from brain tissue. It was identified by its proliferation-enhancing activities for murine fibroblasts, such as 3T3 cells. Due to its basic pI the factor was named basic FGF (bFGF, or HBGF-2, heparin-binding growth factor-2) and is now generally referred to as FGF-2. This is the prototype of the FGF family.

Another type of FGF, also initially isolated from brain tissues, is acidic FGF (aFGF, also known as HBGF-1, heparin-binding growth factor-1 or HBGF-α, heparin-binding growth factor-α), now generally referred to as FGF-1. It was identified by its proliferation-enhancing activity for myoblasts.

Other fibroblast growth factors belonging to the same family include FGF-3 (or HBGF-3, heparin-binding growth factor-3, originally called int-2; see Fekete, *Trends in Neurosci.* 23:332 (2000)), FGF-4 (HBGF-4, heparin-binding growth factor-4, initially recognized as the product of the oncogene hst; see Sakamoto et al., *Proc. Natl. Acad. Sci. USA* 91:12368-72), and FGF-5 (originally called HBGF-5, see Bates et al. Biosynthesis of human fibroblast growth factor 5. *Mol. Cell. Biol.* 11:1840-1845 (1991)); Burgess and Maciag, The heparin-binding (fibroblast) growth factor family of proteins. *Ann. Rev. Biochem.* 58: 575-606 (1989); and Zhan et al. The human FGF-5 oncogene encodes a novel protein related to fibroblast growth factors. *Mol. Cell. Biol.* 8:3487-3495 (1988)).

FGF-6 is also known as HBGF-6, and sometimes called hst-2 or oncogene hst-1 related growth factor, see Iida et al. Human hst-2 (FGF-6) oncogene: cDNA cloning and characterization. *Oncogene* 7:303-9 (1992); and Marics et al. Characterization of the HST-related FGF-6 gene, a new member of the fibroblast growth factor gene family. Oncogene 4:335-40 (1989).

FGF-7 or K-FGF is also known as KGF or keratinocyte growth factor (See Aaronson et al. Keratinocyte growth factor is a fibroblast growth factor family member with unusual target cell specificity. *Annals NY Acad. Sci.* 638:62-77 (1991)); Finch et al. Human KGF is FGF-related with properties of a paracrine effector of epithelial cell growth. *Science* 245:752-5 (1989); Marchese et al. Human keratinocyte growth factor activity on proliferation and differentiation of human keratinocytes: differentiation response distinguishes KGF from EGF family. *J. Cellular Physiol.* 144: 326-32 (1990)).

FGF-8 was found to be identical to androgen-induced growth factor, AIGF and has been well studied (See Blunt et al. Overlapping expression and redundant activation of mesenchymal fibroblast growth factor (FGF) receptors by alternatively spliced FGF-8 ligands. *J. Biol. Chem.* 272:3733-8 (1997)); Dubrulle et al. FGF signaling controls somite boundary position and regulates segmentation clock control of spatiotemporal Hox gene activation. *Cell* 106:219-232 (2001); Gemel et al. Structure and sequence of human FGF8. *Genomics* 35:253-257 (1996); Tanaka et al. A novel isoform of human fibroblast growth factor 8 is induced by androgens and associated with progression of esophageal carcinoma. *Dig. Dis. Sci.* 46:1016-21 (2001)).

FGF-9 was originally called glia activating factor, or HBGF-9. See Miyamoto et al. Molecular cloning of a novel cytokine cDNA encoding the ninth member of the fibroblast growth factor family, which has a unique secretion pattern. *Mol. Cell. Biol.* 13:4251-9 (1993); and Naruo et al. Novel secretory heparin-binding factors from human glioma cells (glia-activating factors) involved in glial cell growth. *J. Biol. Chem.* 268: 2857-64 (1993).

FGF-10 is also called KGF-2, keratinocyte growth factor-2 (see Kok et al. Cloning and characterization of a cDNA encoding a novel fibroblast growth factor preferentially expressed in human heart. *Biochem. Biophys. Res. Comm.* 255:717-721, (1999)).

Several FGF-related factors have been described as fibroblast growth factor homologous factors (FHFs) and are also referred to as FGF-11 (FHF-3), FGF-12 (FHF-1), FGF-13 (FHF-2, see Greene et al. Identification and characterization of a novel member of the fibroblast growth factor family. *Eur. J. Neurosci.* 10:1911-1925 (1998)), and FGF-14 (FHF-4).

FGF-15 is expressed in the developing nervous system and was identified as a gene regulated by transcription factor E2A-Pbx1. McWhirter et al. A novel fibroblast growth factor gene expressed in the developing nervous system is a downstream target of the chimeric homeodomain oncoprotein E2A-Pbx1. *Development* 124:3221-3232 (1997).

FGF-16 was isolated as a cDNA clone from rat heart by homology-based polymerase chain reaction expressing an FGF of 207 amino acids. FGF-16 is 73% identical to FGF-9. Miyake et al. Structure and expression of a novel member, FGF-16, of the fibroblast growth factor family. *Biochem. Biophys. Res. Commun.* 243:148-152 (1998).

The cDNA encoding FGF-17 was isolated from rat embryos and encodes a protein of 216 amino acids. When expressed in 3T3 fibroblasts, mouse FGF-17 is transforming. During embryogenesis, FGF-17 is expressed at specific sites in forebrain, the midbrain-hindbrain junction, the developing skeleton and in developing arteries. See Hoshikawa et al. Structure and expression of a novel fibroblast growth factor, FGF-17, preferentially expressed in the embryonic brain. *Biochem. Biophys. Res. Commun.* 244:187-191 (1998); and Xu et al. Genomic structure, mapping, activity and expression of fibroblast growth factor 17. *Mechanisms of Development* 83:165-178 (1999).

The cDNA encoding FGF-18 was isolated from rat embryos encoding a protein of 207 amino acids. FGF-18 is a glycosylated protein and is most similar to FGF-8 and FGF-17. Injection of recombinant murine FGF-18 has been shown to induce proliferation in tissues of both epithelial and mesenchymal origin, particularly in liver and small intestine. Recombinant rat FGF-18 induces neurite outgrowth in PC12 cells. Recombinant murine FGF-18 protein stimulates proliferation in NIH 3T3 fibroblasts in vitro in a heparan sulfate-dependent manner. For general information see Hu et al. FGF-18, a novel member of the fibroblast growth factor family, stimulates hepatic and intestinal proliferation. *Mol. Cell. Biol.* 18:6063-6074 (1998); and Ohbayashi et al. Structure and expression of the mRNA encoding a novel fibroblast growth factor, FGF-18. *J. Biol. Chem.* 273:18161-18164 (1998).

FGF-19 is related distantly to other members of the FGF family. FGF-19 mRNA is expressed in several tissues including fetal cartilage, skin, and retina, as well as adult gall bladder. It is overexpressed in a colon adenocarcinoma cell line. FGF-19 is a high affinity, heparin-dependent ligand for the FGF-4 receptor. See Xie et al. FGF-19, a novel fibroblast growth factor with unique specificity for FGFR4. *Cytokine* 11:729-735 (1999).

FGF-20 is expressed in normal brain, particularly the cerebellum, and in some cancer cell lines. FGF-20 mRNA is expressed preferentially in the substantia nigra pars compacta. Recombinant FGF-20 protein induces DNA synthesis in a variety of cell types and is recognized by multiple FGF receptors. FGF-20 functions like an oncogene, causing a transformed phenotype when expressed in the 3T3 fibroblast cell line. These transformed cells are tumorigenic in nude mice. See Jeffers et al. Identification of a novel human fibroblast growth factor and characterization of its role in oncogenesis. *Cancer Res.* 61:3131-8 (2001); and Ohmachi et al. FGF-20, a novel neurotrophic factor, preferentially expressed in the substantia nigra pars compacta of rat brain. *Biochem. Biophys. Res. Commun.* 277:355-60 (2000).

FGF-21 was isolated from mouse embryos. FGF-21mRNA is most abundant in the liver with lower levels in the thymus. FGF-21 is most similar to human FGF-19. See Nishimura et al. Identification of a novel FGF, FGF-21, preferentially expressed in the liver. *Biochim. Biophys. Acta* 1492:203-6 (2000).

The cDNA encoding FGF-22 (170 amino acids) was isolated from human placenta. FGF-22 is most similar to FGF-10 and FGF-7. Murine FGF-22 mRNA is expressed preferentially in the skin. FGF-22 mRNA in the skin is found preferentially in the inner root sheath of the hair follicle. See Nakatake et al. Identification of a novel fibroblast growth factor, FGF-22, preferentially expressed in the inner root sheath of the hair follicle. *Biochim. Biophys. Acta* 1517:460-3 (2001).

FGF-23 is most similar to FGF-21 and FGF-19. The human FGF-23 gene maps to chromosome 12p13 linked to human FGF-6 gene. FGF-23 mRNA is expressed mainly in the brain (preferentially in the ventrolateral thalamic nucleus) and thymus at low levels. Missense mutations in the FGF-23 gene have been found in patients with autosomal dominant hypophosphataemic rickets. Overproduction of FGF23 causes tumor-induced osteomalacia, a paraneoplastic disease characterized by hypophosphatemia caused by renal phosphate wasting. See Yamashita et al. Identification of a novel fibroblast growth factor, FGF-23, preferentially expressed in the ventrolateral thalamic nucleus of the brain. *Biochem. Biophys. Res. Commun.* 277:494-8 (2000); and Shimada et al. Cloning and characterization of FGF23 as a causative factor of tumor-induced osteomalacia. *Proc. Natl. Aced. Sci. (USA)* 98:6500-5 (2001).

HBBM (Heparin-binding brain mitogen) was isolated initially as a heparin binding protein from brain tissues of several species and is identical to heparin-binding neurite promoting factor. See Huber et al. Amino-terminal sequences of a novel heparin-binding protein with mitogenic activity for endothelial cells from human bovine, rat, and chick brain: high interspecies homology. *Neurochem. Res.* 15:435-439 (1990).

HB-GAF (heparin-binding growth associated factor) is a neurotrophic and mitogenic factor identical to HBNF (heparin-binding neurite-promoting factor). See Kuo et al. Characterization of heparin-binding growth-associated factor receptor in NIH 3T3 cells. *Biochem. Biophys. Res. Commun.* 182:188-194 (1992).

HB-EGF (heparin-binding EGF-like factor) is found in conditioned media of cell line U937 and is also synthesized by macrophages and human vascular smooth muscle cells. HB-EGF is a monomeric heparin-binding O-glycosylated protein of 86 amino acids and is processed from a precursor of 208 amino acids. Several truncated forms of HB-EGF have been described. HB-EGF is a potent mitogen for NIH 3T3 cells, keratinocytes and smooth muscle cells, but not for endothelial cells. The mitogenic activity on smooth muscle cells is much stronger than for EGF and appears to involve interactions with cell surface heparan sulfate proteoglycans. HB-EGF is a major growth factor component of wound fluid and may play an important role in wound healing. See Abraham et al. Heparin-binding EGF-like growth factor: characterization of rat and mouse cDNA clones, protein domain conservation across species, and transcript expression in tissues. *Biochem. Biophys. Res. Commun.* 190:125-133 (1993); Higashiyama et al. A heparin-binding growth factor secreted by macrophage-like cells that is related to EGF. *Science* 251:936-9 (1991); and Marikovsky et al. Appearance of heparin-binding EGF-like growth factor in wound fluid as a response to injury. *Proc. Natl. Acad. Sci.* (USA) 90:3889-93.

HB-GAM (heparin-binding growth associated molecule) also referred to as HBNF (heparin-binding neurite promoting factor) is a protein of 15.3 kDa isolated as a heparin binding protein from brain tissues of several species. HB-GAM promotes growth of SW-13 cells in soft agar. Courty et al. Mitogenic properties of a new endothelial cell growth factor related to pleiotrophin. *Biochem. Biophys. Res. Commun.* 180: 145-151 (1991); and Hampton et al. Structural and functional characterization of full-length heparin-binding growth associated molecule. *Mol. Biol. Cell.* 3:85-93 (1992).

TGF-beta (TGF-β) exists in at least five isoforms, known TGF-β1, TGF-β2, TGF-β3, TGF-β4 and TGF-β5, all of which are not related to TGF-α. Their amino acid sequences display homologies on the order of 70-80 percent. TGF-β1 is the prevalent form and is found almost ubiquitously while the other isoforms are expressed in a more limited spectrum of cells and tissues.

TGF-beta is the prototype of a family of proteins known as the TGF-beta superfamily. This family includes inhibins, Activin A, MIS (Mullerian activating substance) and BMPs (Bone morphogenic proteins). Burt, Evolutionary grouping of the transforming growth factor-beta superfamily. *Biochem. Biophys. Res. Commun.* 184:590-5 (1992).

EXAMPLES

Example 1

A synthetic HBGF analog was synthesized by standard solid phase peptide synthesis methods. The FGF receptor binding amino acid sequence of the two X region sequences is RKLAVYWSSYKRSRY (SEQ ID NO:65), a modified reverse sequence derived from FGF-2. The peptide was assembled stepwise by solid-phase synthesis on a substituted benzhydrylamine resin, using Fmoc chemistry for temporary protection of amino groups in the repetitive cycles. Branching of the chain was accomplished by stepwise growth of identical chains from the side-chain amino groups of consecutive lysyl residues separated by three aminohexanoic acid residues. The completed peptide chains were cleaved from the resin as C-terminal amides by acidolysis, which also removed the acid-labile side-chain protecting groups.

The crude peptide preparation was first purified by heparin affinity chromatography. The crude preparation was solubilized in 10 mM HEPES (pH 7.0), loaded onto a HiTrap® Heparin HP column (Amersham Pharmacia Biotech, Piscataway, N.J., USA), and washed with 10 column volumes of 10 mM HEPES (pH 7.0). The peptide was then eluted with 2 M NaCl in 10 mM HEPES (pH 7.0), monitored by 280 nm absorbance. Peptide fractions were desalted and concentrated by loading onto Sep-Pak® C18 cartridges (Waters, Milford, Mass., USA), washed with 10 column volumes of water, and then eluted with 80% acetonitrile. Eluted fractions were lyophilized, redissolved in water, and the concentration was determined by BCA® Protein Assay Kit (Pierce Endogen, Rockford, Ill., USA) using bovine serum albumin as a reference.

The resulting analog had the following structure:

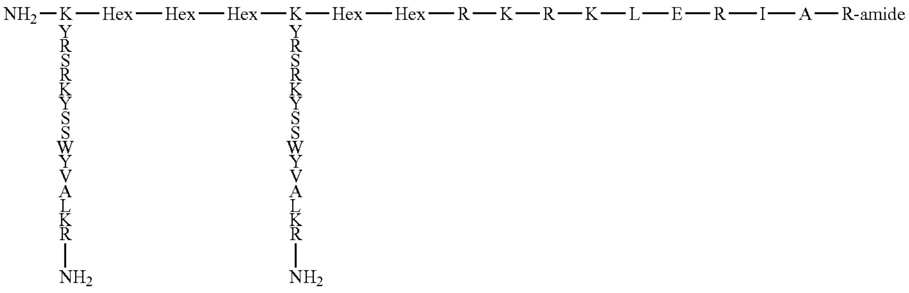

In the foregoing structure, "Hex" is aminohexanoic acid.

Example 2

A synthetic HBGF analog was synthesized by standard solid phase peptide synthesis methods. The amino acid sequences corresponding to regions Y and Z of formula II are identical to those of the analog described in Example 1. The receptor binding amino acid sequence of the two X region sequences is WDNWGVDSFDVYL (SEQ ID NO:60), a reverse sequence derived from BMP.

The crude preparation was purified as described above in Example 1. The resulting analog had the following structure:

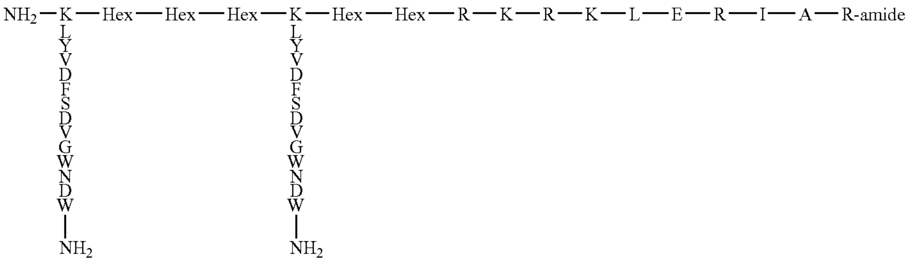

Example 3

A synthetic HBGF analog was synthesized by standard solid phase peptide synthesis methods. The amino acid sequences corresponding to regions Y and Z of formula II are identical to those of the analog described in Example 1. The receptor binding amino acid sequence of the two X region sequences is LVVKENEDLYLMSIA (SEQ ID NO:57), a reverse sequence derived from BMP.

The crude preparation was purified as described above in Example 1. The resulting analog had the following structure:

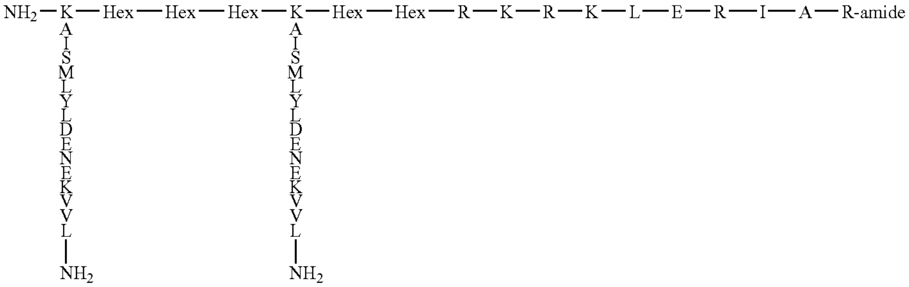

Example 4

A synthetic HBGF analog is synthesized by standard solid phase peptide synthesis methods as in Example 1. The FGF receptor binding amino acid sequence of the two X region sequences is YRSRKYTSWYVALKR (SEQ ID NO:7). The peptide is assembled stepwise by solid-phase synthesis on a substituted benzhydrylamine resin, using Fmoc chemistry for temporary protection of amino groups in the repetitive cycles. Here Y is the three aminohexanoic acid residues. Branching of the chain is accomplished by stepwise growth of identical chains from the side-chain amino groups of consecutive lysyl residues separated by two aminohexanoic acid residues. The completed peptide chains are cleaved from the resin as C-terminal amides by acidolysis, which also removes the acid-labile side-chain protecting groups. The resulting analog had the following structure:

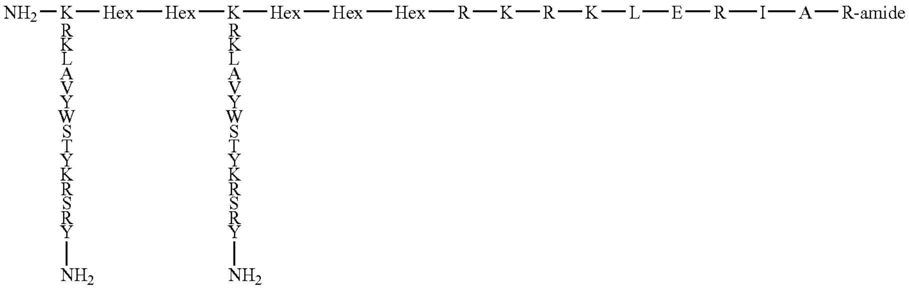

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound of formula II:

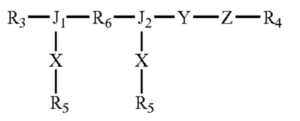

II wherein:

$R_3$ and $R_5$ are each independently $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or is amino acid, a dipeptide or a tripeptide with an N-terminus $NH_2$, $NH_3^+$, or NH group or a corresponding acylated derivative;

$R_4$ is —OH, $NH_2$, NH—$R_7$, or is an amino acid, a dipeptide or a tripeptide with a C-terminus —OH, $NH_2$, or NH—$R_7$;

$R_7$ is an aliphatic $C_1$ to $C_{17}$ chain;

each X comprises a sequence selected from SEQ ID NO:57, SEQ ID NO:58, and SEQ ID NO:64;

$J_1$ and $J_2$ are each independently a trifunctional alpha amino acid residue, wherein each X is covalently bonded through a side chain of $J_1$ or $J_2$;

$R_6$ is a linker comprising a chain from 1 to about 20 backbone carbons covalently bonded to $J_1$ and $J_2$;

Y is a linker comprising a chain from 0 to about 50 backbone carbons covalently bonded to $J_2$ and Z; and Z is SEQ ID NO:2.

2. The compound of claim 1 wherein $R_6$ further comprises a linker that is not found in the natural ligand of the heparin-binding growth factor receptor (HBGFR) which X binds.

3. The compound of claim 1 wherein Y further comprises a linker that (i) hydrophobic, (ii) comprises a chain of a minimum of about 9 and a maximum of about 50 carbons, and (iii) is not found in the natural ligand of the heparin-binding growth factor receptor (HBGFR) which X binds.

4. The compound of claim 1 wherein $J_1$ and $J_2$ are diamine amino acid residues selected from the group consisting of 2,3 diamino propionyl amino acid, 2,4, diamino butylic amino acid, lysine and ornithine.

5. The compound of claim 1 wherein the covalent bond between X and $J_2$ comprises an amide, disulfide, thioether, Schiff base, reduced Schiff base, imide, secondary amine, carbonyl, urea, hydrazone or oxime bond.

6. The compound of claim 1 wherein the side chains of $J_1$ and $J_2$ comprise a reactive carboxyl group.

7. The compound of claim 1 of formula III:

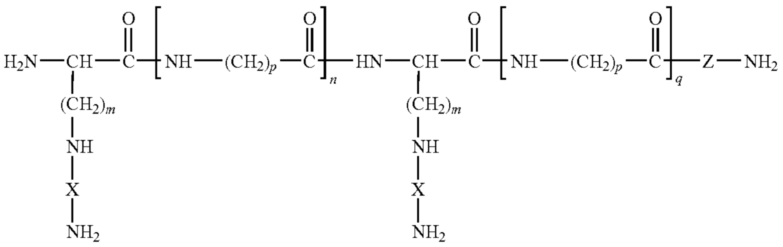

III wherein each m is independently from 1 to about 10, n is from 1 to about 6, each p is independently from 1 to about 10, q is from 1 to about 20, and X and Z are as defined in claim 1.

8. The compound of claim 7 wherein Y comprises $[NH_2-(CH_2)_pCO]_q$ wherein p is from 1 to about 10 and q is from 1 to about 20.

9. A pharmaceutical composition comprising The compound of claim 1 or a pharmaceutically acceptable salt thereof and a pharmaceutical carrier.

* * * * *

UNITED STATES PATENT AND TRADEMARK OFFICE

CERTIFICATE OF CORRECTION

PATENT NO. : 7,598,224 B2
APPLICATION NO. : 11/065970
DATED : October 6, 2009
INVENTOR(S) : Zamora et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 342 days.

Signed and Sealed this

Twenty-eighth Day of September, 2010

David J. Kappos
*Director of the United States Patent and Trademark Office*